(12) United States Patent
Buck et al.

(10) Patent No.: US 8,452,953 B2
(45) Date of Patent: May 28, 2013

(54) INSULIN PUMP PROGRAMMING SOFTWARE FOR SELECTIVELY MODIFYING CONFIGURATION DATA

(75) Inventors: Schuyler Buck, Muncie, IN (US); Jason Bush, Fishers, IN (US); Kristin Davenport, Fortville, IN (US); Alan Greenburg, Indianapolis, IN (US); Robert Hellwig, Bern (CH); David Bradley Markisohn, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 915 days.

(21) Appl. No.: 12/205,600

(22) Filed: Sep. 5, 2008

(65) Prior Publication Data
US 2010/0077198 A1     Mar. 25, 2010

(51) Int. Cl.
G06F 15/177     (2006.01)
(52) U.S. Cl.
USPC .............................................. 713/100; 713/1
(58) Field of Classification Search
USPC .................................................. 713/1, 2, 100
See application file for complete search history.

(56) References Cited

U.S. PATENT DOCUMENTS

| | | | | |
|---|---|---|---|---|
| 6,493,549 | B1 * | 12/2002 | Axelson et al. | 455/419 |
| 6,850,157 | B1 * | 2/2005 | Yamamoto et al. | 340/539.1 |
| 7,535,254 | B1 * | 5/2009 | Case | 326/39 |
| 2003/0163223 | A1 | 8/2003 | Blomquist | |
| 2004/0103897 | A1 * | 6/2004 | Hickle et al. | 128/204.23 |
| 2005/0033385 | A1 * | 2/2005 | Peterson et al. | 607/60 |
| 2005/0053023 | A1 * | 3/2005 | Rajkotia et al. | 370/312 |
| 2007/0016449 | A1 | 1/2007 | Cohen et al. | |
| 2007/0033074 | A1 | 2/2007 | Nitzan et al. | |
| 2007/0066956 | A1 | 3/2007 | Finkel | |
| 2007/0106135 | A1 | 5/2007 | Sloan et al. | |
| 2007/0112298 | A1 | 5/2007 | Mueller, Jr. et al. | |
| 2007/0124002 | A1 | 5/2007 | Estes et al. | |
| 2008/0089302 | A1 * | 4/2008 | Godfrey et al. | 370/338 |
| 2009/0164251 | A1 * | 6/2009 | Hayter | 705/3 |

OTHER PUBLICATIONS

Disetronic, "DiaLog Pump Programming Tool," Reference Manual, ver. 02 (Jun. 2005).
Medtronic Minimed, "Solutions Pumps and Meters Software," Manual, ver. 7.0 (2005).
Disetronic Medical Systems AG, "Accu-Chek Insulin Pump Configuration Software," User Manual, (2005).
Animans Corporation, "ezManager Plus," User Manual, (2007).

* cited by examiner

*Primary Examiner* — Paul Yanchus, III
(74) *Attorney, Agent, or Firm* — Faegre Baker Daniels LLP

(57) ABSTRACT

Insulin pump programming software is disclosed that permits selectively modifying insulin pump configuration files. The software facilitates retrieving a source file consisting of a configuration file or portion thereof from a source location. The source file may include general configuration data and insulin delivery data. Once retrieved, the source file may be edited, then the entire source file or a portion thereof may be saved to a target configuration file at one or more target locations. Only the portion of the target configuration file corresponding to the saved source file or portion thereof is replaced by the source file.

4 Claims, 26 Drawing Sheets

INSULIN PUMP PROGRAMMING SOFTWARE FOR SELECTIVELY MODIFYING CONFIGURATION DATA

FIELD OF THE INVENTION

The present teachings generally relate to programming insulin pumps and more specifically to pump programming software that permits selective reading and writing of all or portions of data included in insulin pump configuration files.

BACKGROUND

An insulin pump is a fluid infusion device for delivering insulin to people who suffer from diabetes. The pump, which is worn by the user and eliminates the need for multiple daily insulin injections, closely imitates a normally functioning pancreas by releasing hundreds of small doses of insulin each day into the body through an infusion set to regulate blood glucose levels. The rate of delivery of these small doses (i.e., the basal rate) varies from user to user. Indeed, even for a particular user, the basal rate varies throughout the day, and depends upon a variety of factors such as the user's internal clock, metabolism, physical health, and level of stress and exercise.

A basal rate profile consists of one or more basal rates defined to cover the 24 hours of the day (e.g., 24 hourly basal rates). Many users use different basal rate profiles for different circumstances. For example, one basal rate profile may be used for weekdays, another profile (i.e., with different hourly basal rates) for weekends, and another profile for vacation days. These different basal rate profiles are designed to accommodate the expected differences in the user's background insulin needs resulting from variations in the user's sleep patterns, levels of exercise and stress, health condition, menstrual cycle status, etc. during such periods. Pumps also deliver (either automatically or when activated by the user) bolus doses of insulin (in addition to the basal rate) before meals or snacks to compensate for caloric intake.

As the amount and rate of insulin delivery (both basal and bolus) must be tailored to the individual needs of the user, modern pumps are programmable. Some pumps are capable of communicating with a separate computing device, and are compatible with programming software applications that may be executed on the computing device. The programming software permits an operator, such as the user or a health care provider, to customize the settings of the various parameters that affect the pump's operation. These parameters are included in a configuration file that is executed by the pump, and include hourly basal rates, maximum hourly basal rates, bolus dose settings, communication settings, battery settings, and many others. For example, using programming software, a user may upload a configuration file from the user's pump, modify the settings for certain parameters to change the operation of the pump, and save the modified configuration file to the pump. Alternatively, a health care provider responsible for programming the pumps of multiple patients may select an initial generalized configuration file stored in a source location such as a pump or memory location of a computing device as a starting point for programming the patients' pumps. Many of the parameter settings of the initial configuration file (e.g., battery type, language, etc.) may be suitable for all of the pumps to be programmed. Other settings (e.g., hourly basal rates, bolus dose settings, etc.) may be unique to each patient's pump. After the health care provider selects the initial configuration file, he or she may change only the settings needed to customize the pump's operation for the current patient, then save the customized configuration file to the patient's pump without having to define a setting for every pump parameter.

As suggested by the foregoing, insulin pumps perform relatively complex functions, which directly affect the health of the user. For at least these reasons, programming software is generally designed to simplify, to the extent possible, the processes for programming pump functions while simultaneously incorporating safety measures to prevent operators from inadvertently programming a pump with parameter settings that may harm the user or adversely affect the operation of the pump.

As mentioned above, pump programming software can be viewed as communicating with one of two memory locations—pump memories and memory locations on computing devices. Information can be read from either location or written to either location. In general, the most comprehensive set of information either read from or written to memory by pump programming software is the configuration file described above. The above-mentioned parameter settings can be grouped into general configuration data and insulin delivery data. General configuration data includes the settings for parameters such as language choice, volume, backlight duration, and other parameters that do not directly affect the timing and amount of insulin delivery. Insulin delivery data includes the settings for parameters such as hourly basal rate, maximum hourly basal rate, total daily basal dose, temporary basal rate increment and duration, maximum bolus dose, bolus dose increment, and other parameters relating directly to insulin delivery. One common sub-set of insulin delivery data is the basal rate profile referred to above. Each profile includes one or more basal rates defined to cover the 24 hours of the day (e.g., 24 hourly basal rates), a maximum hourly basal rate value that functions as the upper limit on the degree to which the hourly basal rates may be adjusted by an operator, and a daily basal insulin total value that reflects the sum of the basal insulin delivered by the profile. As indicated above, users typically use a plurality of different basal rate profiles depending upon their anticipated condition/activities for the day (i.e., weekday, weekend, vacation, illness, etc.). Accordingly, a typical configuration file includes a set of basal rate profiles for selection by the user.

In at least one sense, the more surgical or selective the communications with a pump or file the better. In other words, it is desirable to read or write the least comprehensive set of information needed to implement the desired change in pump operation. If changes are to be made to both the general configuration data and the insulin delivery data, it may be desirable to communicate the entire configuration file. If changes are to be made to a configuration file that affect all of the profiles in a set of basal rate profiles, but do not affect the general configuration data, then it may be desirable to communicate only the set of basal rate profiles. Finally, if changes are to be made to a configuration file that only affect a single profile of the set of basal rate profiles, then it may be desirable to communicate only the affected basal rate profile. Moreover, in the course of making changes to pump configuration files, it is desirable to require the operator to carefully consider whether the changes selected are exactly what the operator intended, especially changes that may adversely affect the health of the user.

SUMMARY

The present approach to pump programming software permits the operator to select a configuration file, a set of basal rate profiles, or a single basal rate profile to be made active as a source file for subsequent programming. The active file may be retrieved from either a pump or a memory location on a computing device. The software permits editing of the source file and saving it to a target location. If the source file is a configuration file, the software facilitates saving any of the following to the target location: the entire configuration file, the set of profiles in the configuration file, or a single profile of the set of profiles. If the source file is a set of profiles, the software facilitates saving either the set of profiles or a single profile of the set of profiles to the target location. The target location may be a pump memory, a memory location on a computing device, or both. This approach may reduce the time required for data transfer during pump programming, the probability for interruptions during the data transfer, and the likelihood of programming a pump with invalid or unintended data.

Additionally, when programming changes to a pump configuration file that are critical to the safe operation of the pump, the software requires two levels of confirmation before completing the programming process.

In an exemplary embodiment of the present disclosure, there is provided a method for selectively modifying insulin pump configuration files. The method includes the step of retrieving a source configuration file from a source location. The source configuration file includes general configuration data and at least one basal rate profile. The method further includes the step of selecting a target configuration file including general configuration data and at least one basal rate profile. Finally, the method includes the step of saving the at least one basal rate profile retrieved from the source configuration file to the target configuration file without modifying the general configuration data of the target configuration file. In a variation thereof, the method also includes the step of editing the at least one basal rate profile retrieved from the source configuration file. In another variation, the source location is a memory location of an insulin pump and the target configuration file is stored on an insulin pump. In a further variation, the saving step includes the step of replacing at least one basal rate profile included in the target configuration file with the at least one basal rate profile retrieved from the source configuration file. In an extension of the previous variation, the saving step further includes the step of reviewing on a display a comparison of the at least one basal rate profile retrieved from the source configuration file to the at least one basal rate profile included in the target configuration file. In a still further extension, the saving step includes the step of inputting at least two confirmation inputs when a critical parameter relating to the at least one basal rate profile included in the target configuration file is to be increased.

In another exemplary embodiment of the present disclosure, there is disclosed a system for programming an insulin pump. The system includes a computing device, a communication link between the computing device and the insulin pump, and software for execution by the computing device. The software is configured to facilitate retrieval of a source configuration file from a source location. The source configuration file includes general configuration data and a set of individual basal rate profiles. The software has a first mode wherein the source configuration file is written to a target configuration file having general configuration data and a set of individual basal rate profiles, a second mode wherein the set of profiles of the source configuration file is written to the target configuration file without writing the general configuration data of the source configuration file, and a third mode wherein one of the profiles of the set of profiles of the source configuration file is written to target configuration file without writing the general configuration data and the other of the profiles of the set of profiles of the source configuration file. In a variation thereof, the software is further configured to retrieve the set of profiles from the source configuration file without retrieving the general configuration data. In another variation, the software is further configured to retrieve one of the profiles of the set of profiles from the source configuration file without retrieving the general configuration data and the other of the profiles of the set of profiles. In another variation, the source location is a memory location of the computing device and the target configuration file is stored on the insulin pump. In yet another variation of the disclosed system, the target configuration file includes a first configuration file stored on the insulin pump and a second configuration file stored in a memory location of the computing device.

In yet another exemplary embodiment of the present disclosure, a method is disclosed of programming an insulin pump that operates in accordance with general configuration data and basal rate profile data contained in a configuration file stored in a memory of the pump. The method includes the step of executing software on a computing device to obtain new basal rate profile data from a source location. The method further includes the step of providing input to the computing device corresponding to a command to the software to replace at least a portion of the profile data with the new profile data without modifying the general configuration data contained in the configuration file. Finally, the method includes the step of reviewing on a display of the computing device differences between the profile data and the new profile data. In a variation of the disclosed method, the profile data includes a plurality of different basal rate profiles. In another variation, the new profile data consists of a single basal rate profile. In yet another variation, the source location is a memory location of the computing device. In still another variation, the source location is a memory location on a second pump.

In another exemplary embodiment of the present disclosure, there is disclosed a computer readable medium tangibly embodying a program of instructions executable by a computing device to perform method steps for managing configuration files including general configuration data and basal rate profile data. The method steps include the step of providing an operator a first option for retrieving basal rate profile data from a first source configuration file stored on an insulin pump without retrieving general configuration data from the first source configuration file. The method steps further include the step of providing the operator a second option for retrieving basal rate profile data from a second source configuration file stored on a computing device without retrieving general configuration data from the first source configuration file. The method steps further include the step of providing the operator a third option for saving retrieved basal rate profile data to a first target configuration file stored on an insulin pump without modifying the general configuration data in the first target configuration file. Finally, the method steps further include the step of providing the operator a fourth option for saving retrieved basal rate profile data to a second target configuration file stored on a computing device without modifying the general configuration data in the second target configuration file. In a variation thereof, the method steps further include the step of providing the operator a fifth option for initiating a workflow for saving retrieved basal rate profile data to the first and the second target configuration files without modifying the general configuration data of either the first or the second target configuration files by activating a single button. In another variation, the method steps further include the step of causing, upon selection of the third option, a display of differences between the retrieved basal rate profile data and basal rate profile data in the first target configuration file. In an extension of this variation, the causing step further includes the step of prompting the operator to provide a first input to confirm an intention to replace the basal rate profile data in the first target configuration file with the retrieved basal rate profile data. In a further extension, the prompting step further includes the step of requiring the operator to provide a second input to re-confirm the intention to replace the basal rate profile data in the first target configuration file with the retrieved basal rate profile data when a bolus delivery parameter of the retrieved basal rate profile data is greater than a corresponding bolus delivery parameter of the basal rate profile data in first target configuration file. In another extension, the prompting step further includes the step of requiring the operator to provide a second input to re-confirm the intention to replace the basal rate profile data in the first target configuration file with the retrieved basal rate profile data when a daily basal insulin total parameter of the retrieved basal rate profile data is greater than a corresponding daily basal insulin total parameter of the basal rate profile data in first target configuration file. In a still further extension, the second input includes keyboard entry of the daily basal insulin total parameter of the retrieved basal rate profile data into a data field. In another variation, the first and the second option each include the option of retrieving one of an basal rate profile set and a single basal rate profile.

In still another exemplary embodiment of the present disclosure, there is disclosed a system for programming an insulin pump. The system includes means for retrieving a source configuration file from a source location, wherein the source configuration file includes general configuration data and a set of individual basal rate profiles. The system also includes means for saving the source configuration file to a target configuration file having general configuration data and a set of individual basal rate profiles. The system further includes means for saving the set of profiles of the source configuration file to the target configuration file without writing the general configuration data of the source configuration file. Finally, the system also includes means for saving one of the profiles of the set of profiles of the source configuration file to the target configuration file without writing the general configuration data and the other of the profiles of the set of profiles of the source configuration file.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, wherein.

Corresponding reference characters indicate corresponding parts throughout the several views.

DETAILED DESCRIPTION

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

It should be understood that although the concepts below are described as relating to insulin pump configuration software, such as the ACCU-CHEK® Insulin Pump Configuration Software provided by Roche Diagnostics Corporation, the concepts may also relate to diabetes management software systems for tracking and analyzing health data, such as, for example, the ACCU-CHEK® 360° product provided by Roche Diagnostics Corporation. Moreover, the concepts described herein may also have applicability to apparatuses, methods, systems, and software in fields that are unrelated to healthcare. Furthermore, it should be understood that references in this patent application to devices, pumps, meters, monitors, or related items are intended to encompass any currently existing or later developed apparatus that includes some or all of the features attributed to the referred to apparatus, including but not limited to the ACCU-CHEK® Active, ACCU-CHEK® Aviva, ACCU-CHEK® Compact, ACCU-CHEK® Compact Plus, ACCU-CHEK® Integra, ACCU-CHEK® Go, ACCU-CHEK® Performa, ACCU-CHEK® Spirit, ACCU-CHEK® D-Tron Plus, and ACCU-CHEK® Voicemate Plus, all provided by Roche Diagnostics Corporation or divisions thereof.

Figure 1:
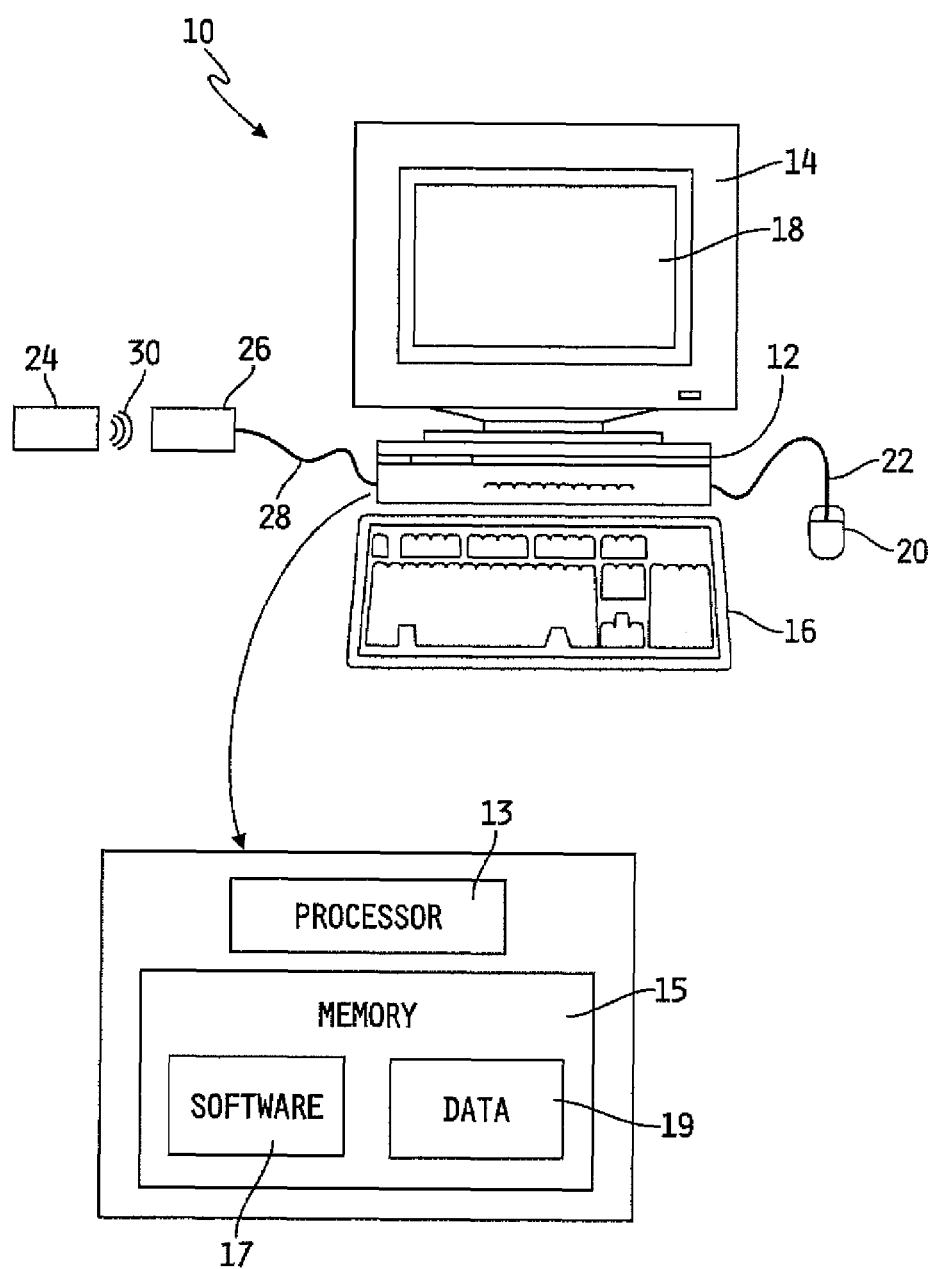
FIG. 1 is a conceptual diagram of a computing device in communication with an insulin pump.

Turning now to the figures, FIG. 1 depicts an exemplary embodiment of a system 10, some or all of the components of which may be used in conjunction with the teachings of the present disclosure. System 10 generally includes a computing device 12, shown here in the form of a computer having display device 14, in this case a computer video screen or monitor having screen 18, a keyboard 16, a processor 13, and memory 15, which may contain the software 17 of the present disclosure and data 19 as is further described herein. While described and depicted herein with specific reference to a computer, certain concepts of the present disclosure may be utilized in conjunction with any computing device capable of operating pump programming software. Computing device 12 also has a pointing device or mouse 20 connected to it by cable 22 (or wirelessly). While mouse 20 and keyboard 16 are shown, system 10 may include any input device such as a touchpad, joystick, touch screen, trackball, etc.

Computing device 12 may include a variety of computer-readable media. Computer-readable media can be any available media that can be accessed by computing device 12 and includes both volatile and non-volatile media, and removable and non-removable media. By way of example, and not limitation, computer-readable media may comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules and other data and which can be accessed by computing device 12. Computer-readable media may be accessed directly or through a network such as the Internet.

System 10 is configured to provide information to, and receive information from, infusion pump 24. Again, while an infusion pump, and more particularly an insulin pump, is described herein, it should be understood that the teachings of the present disclosure may also apply to devices such as "smart" insulin pens or other such devices known or hereafter developed. In FIG. 1, computing device 12 is shown coupled to communication media or dongle 26, in this case a modulated signal transceiver, accessible to computing device 12 by means of cable 28, and configured to transmit and receive modulated signal 30 to establish logical communication with pump 24. In another exemplary embodiment, computing device 12 and pump 24 may include ports configured to establish a physical connection. By way of example, and not limitation, dongle 26 may include wired media such as a wired network or direct wired connection, and wireless media such as acoustic, RF, infrared and other wireless media. More specifically, dongle 26 as depicted includes an infrared port for communication with a similar infrared port of pump 24.

Figure 2:
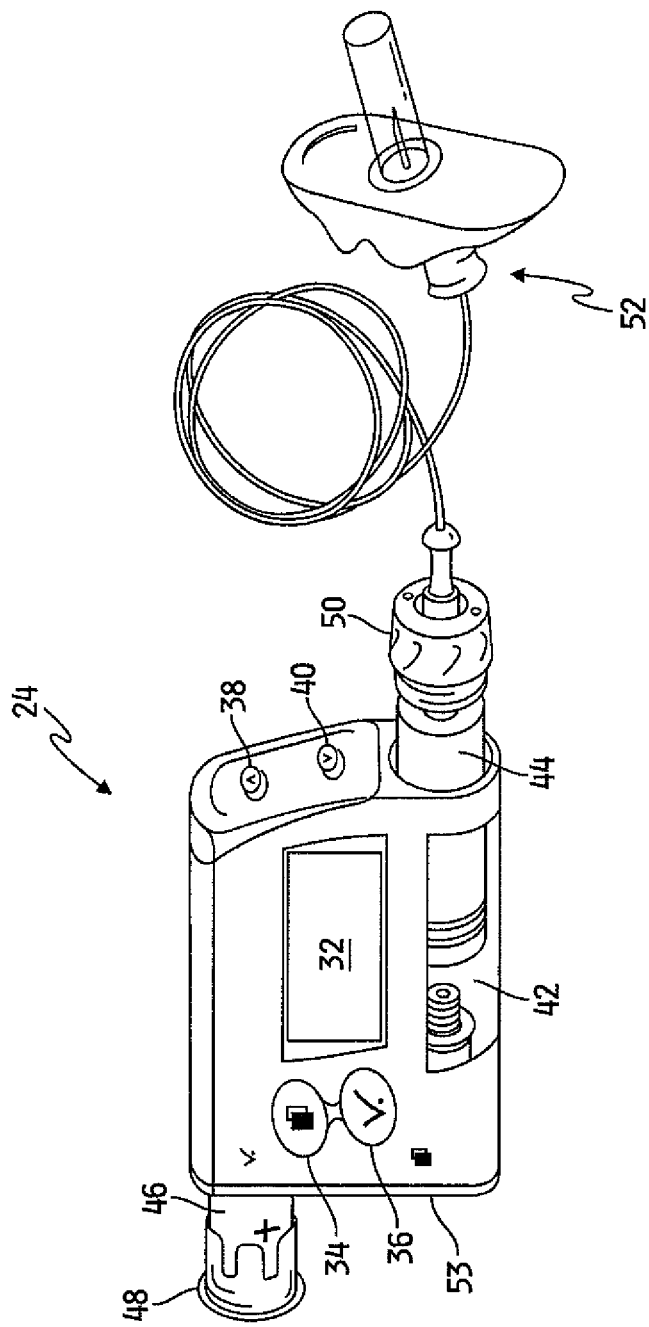
FIG. 2 is perspective view of an insulin pump coupled to an infusion set.

Referring now to FIG. 2, pump 24 includes a display 32 for displaying information to an operator or user, a menu button 34 for navigating though the various functions provided by pump 24, a check button 36 for selecting options, an up key 38 and down key 40 for scrolling through options and controlling certain insulin delivery functions, a cartridge receptacle 42 for storing an insulin cartridge 44, a battery 46 (shown partially inserted), a battery cap 48 (shown unsecured to pump 24), an adapter 50 for physically coupling cartridge 44 to an infusion set 52, and a communication port 53 for sending information to, or receiving information from, computing device 12 through dongle 26.

Figure 3:
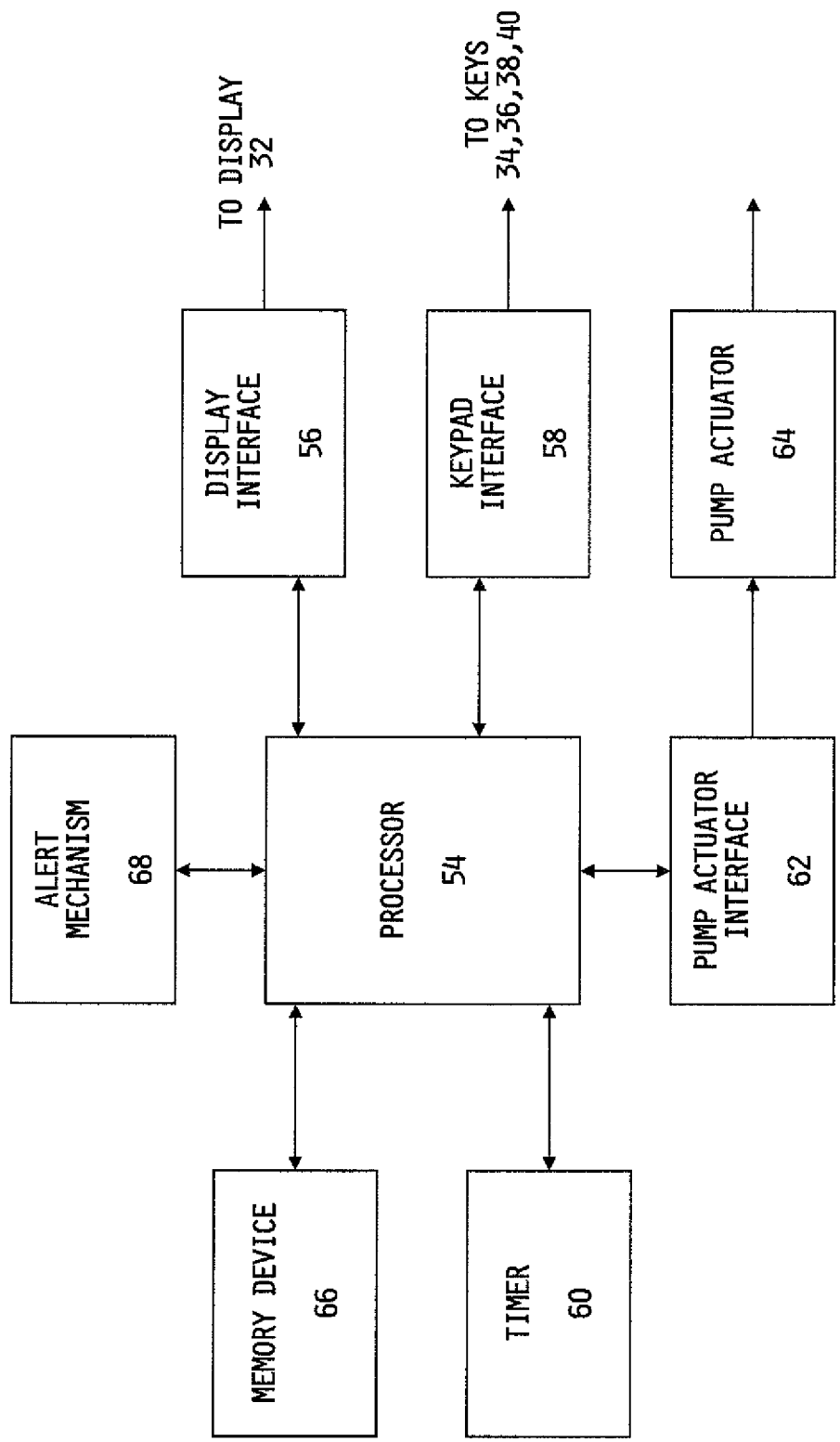
FIG. 3 is a block diagram of internal components of the pump of FIG. 2.

FIG. 3 provides a block diagram representation of internal components of pump 24. As shown, pump 24 includes a processor 54 coupled to a display interface 56, which is coupled to display 32. Processor 54 is also coupled to a keypad interface 58 which is coupled to keys 34, 36, 38, 40, and a pump actuator interface 62 which is coupled to an actuator 64 suitable for delivering insulin doses (medical infusion pumps other than insulin pumps will deliver doses of other medicament). Processor 54 is further coupled to a memory device 66 that stores application programs and data, including the configuration files described herein. Memory device 66 is constructed of any combination of volatile and/or nonvolatile memory suitable for a particular embodiment. Processor 54 is also coupled to an alert mechanism 68, that, in various embodiments is a buzzer, a vibrator, a light emitting diode, or the like, suitable for providing audible, tactile, or visual alerts to an insulin pump user. Finally, processor 54 is coupled to a timer 60, which is capable of maintaining a current time, including time of day and day of the week.

Figure 4:
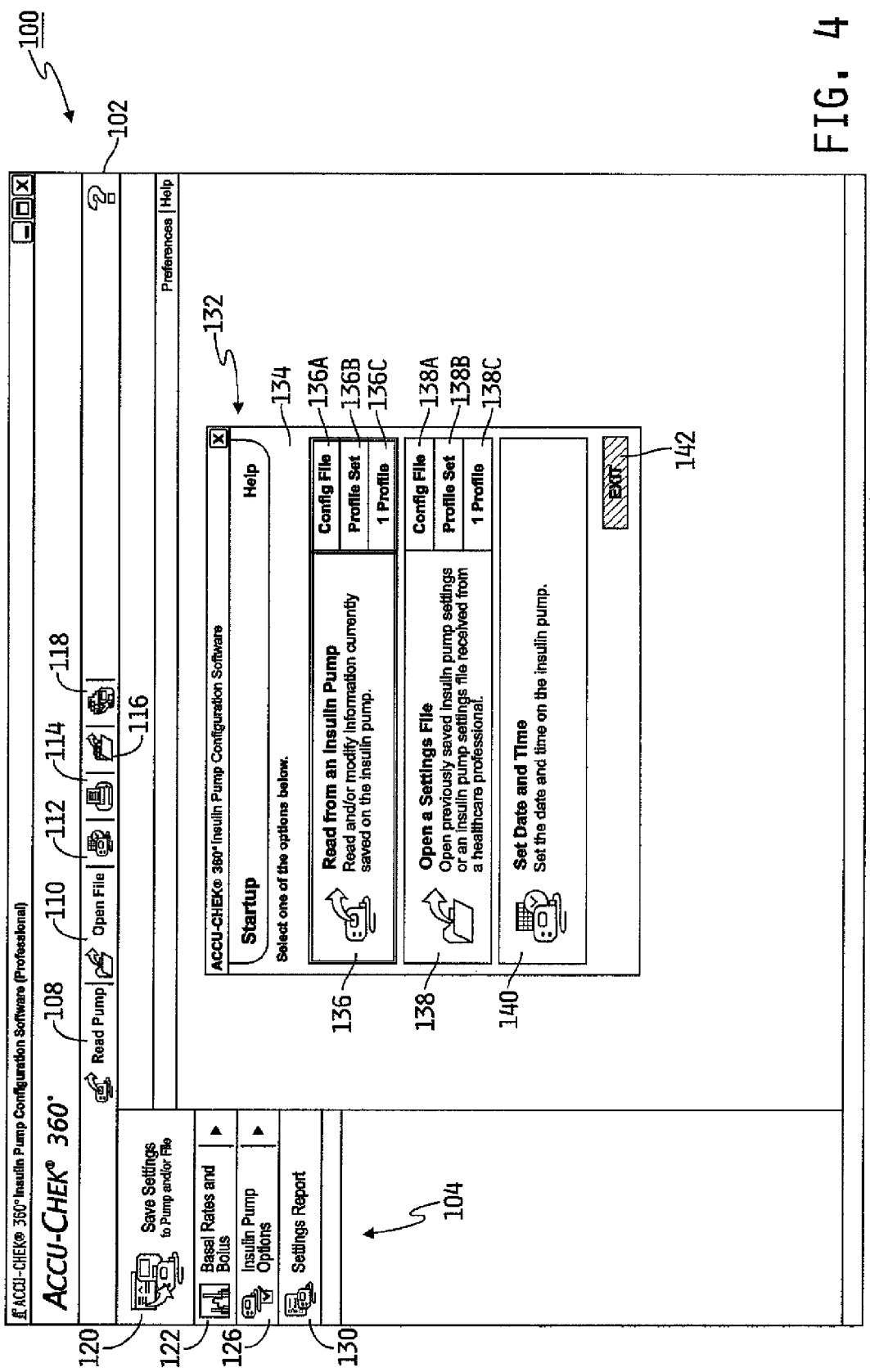
FIG. 4 is a screenshot of a home screen displayed upon activation of software according to teachings of the present disclosure.

FIG. 4 depicts the home screen 100 displayed upon activation of software 17. Home screen 100 generally includes a toolbar 102, a navigation menu 104, and an active window 106. Toolbar 102 includes a read pump icon 108, an open file icon 110, a date/time icon 112, a print icon 114, a load all profiles from file icon 116, and a save all profiles to a file icon 118. Navigation menu 104 includes a save settings button 120, a basal rates and bolus button 122, an insulin pump options button 126, and a settings report button 130. The content of active window 106 changes depending upon the operation being performed by software 17. Here, active window 106 includes a start up dialog box 132.

Start up dialog box 132 includes a message area 134, a read pump area 136 with a configuration file button 136A, a profile set button 136B, and a single profile button 136C, an open area 138 with a configuration file button 138A, a profile set button 138B, and a single profile button 138C, a set date/time button 140, and an exit button 142. For the purpose of this description, the operator will be described as obtaining an insulin pump configuration file 141 from memory 15 (i.e., where it is stored as data 19) of computing device 12 using open configuration file button 138A. It should be understood that the options for retrieving a configuration file, a profile set or a single profile provided by buttons 138A, 138B, and 138C, respectively, are also accessible by activating open file icon 110 on toolbar 102.

As is further described herein, the processes for saving information to pump 24 or to memory 15 on computing device 12 differs. The process for obtaining or retrieving such information from either pump 24 or memory 15 on computing device 12, however, is not meaningfully different for the purpose of the present disclosure. Accordingly, it is sufficient to note that the functions of read pump configuration file button 136A, read pump profile set button 136B, and read pump single profile button 136C (all of which are also accessible by activating read pump icon 108 on toolbar 102) are not expressly described herein except to say that they are similar to the functions of buttons 138A, 138B, and 138C. The operator begins the process of opening configuration file 141 stored in memory 15 by activating open configuration file button 138A.

Figure 5:
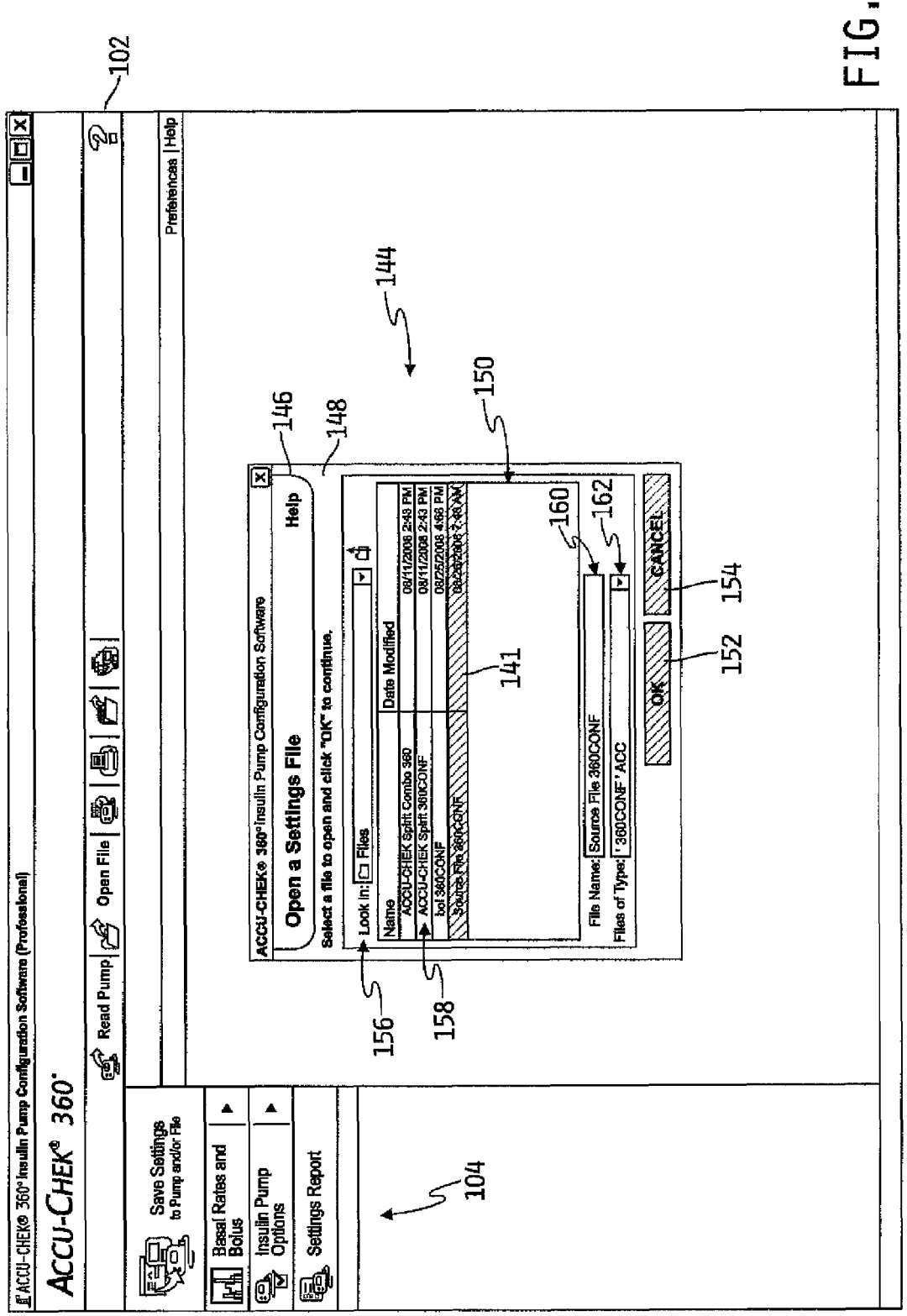
FIG. 5 is a screenshot including an open file dialog box.

As is shown in FIG. 5, when the operator activates open configuration file button 138A, start up dialog box 132 in active window 106 is replaced by open settings file dialog box 144. Open settings dialog box 144 includes a title bar 146 which describes the operation being performed, a message area 148 which provides instructions to the operator for performing the operation, a file selection window 150, an OK button 152 and a cancel button 154. File selection window 150 includes a file location area 156 for defining a folder location of files using a conventional tree structure, a file information area 158 that provides information about the files in the folder selected using file location area 156, a file name area 160 that includes the name of a file selected from file information area 158, and a file type area 162 for limiting, in a conventional manner, the types of files in the currently selected folder to be displayed in the file information area 158. Here, the operator highlights the source file named Source File.360CONF and activates OK button 152 to retrieve configuration file 141.

Figure 6:
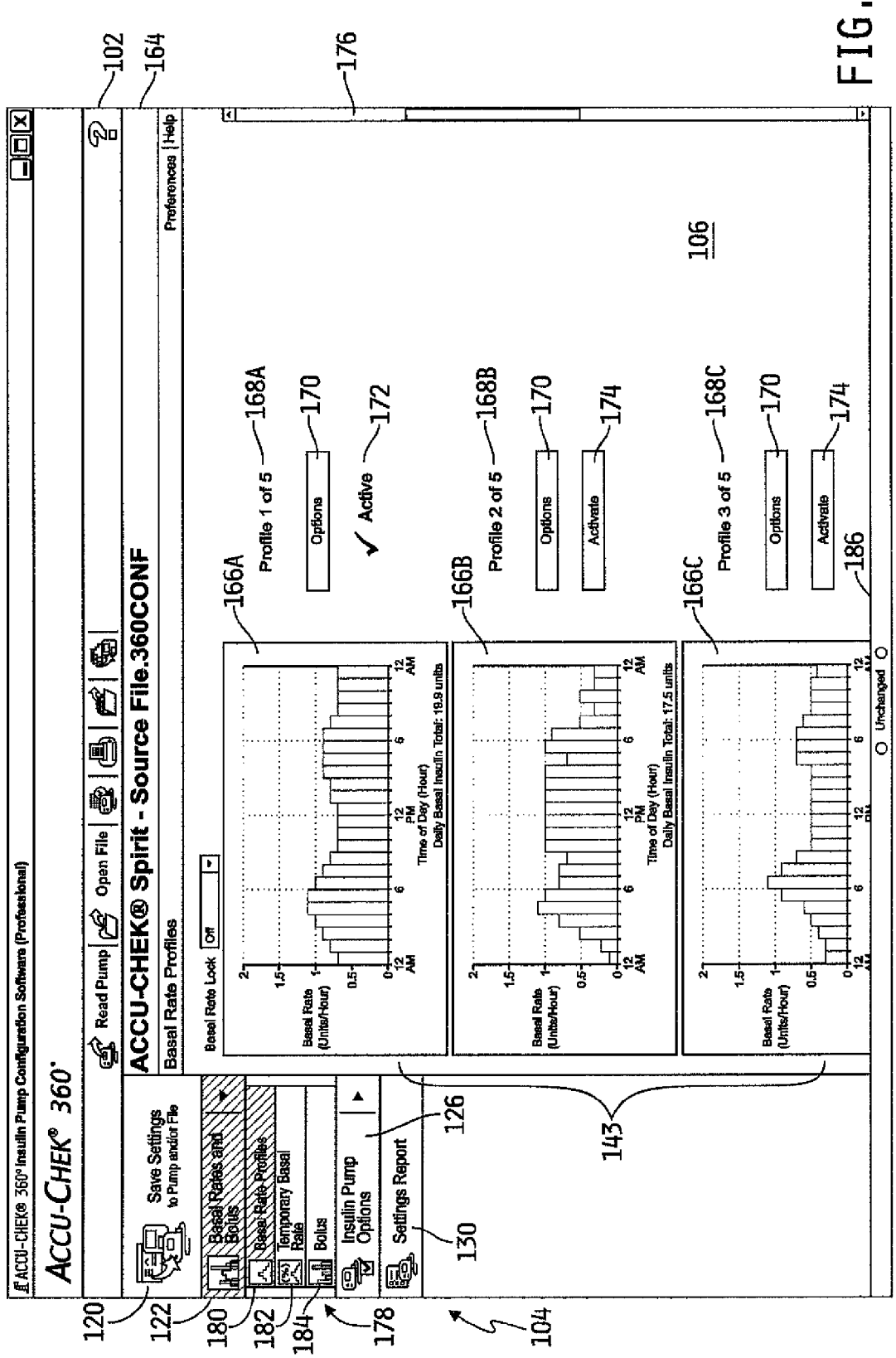
FIG. 6 is a screenshot generated upon activating a configuration file.

After configuration file 141 is retrieved from memory 15 of computing device 12, the operator is provided information in active window 106 regarding the basal rate profiles included in configuration file 141 as depicted in FIG. 6. In the depicted context, active window 106 includes a title bar 164 that identifies the active file (or if the active file is uploaded from pump 24, the pump name and serial number), at least one thumbnail image 166A-C that functions as a graphic preview of the data associated with a basal rate profile included in configuration file 141, at least one profile indicator 168A-C indicating the number of the corresponding basal rate profile represented by the associated thumbnail image 166A-C, at least one options button 170, and an active icon 172 and/or an activate button 174. In one embodiment of the present disclosure, configuration file 141 includes a basal rate profile set 143 consisting of five individual basal rate profiles. Accordingly, as depicted in the figure, a thumbnail image 166A-C, profile indicator 168A-C, options button 170, and an active icon 172 and/or an activate button 174 is displayed for each profile in profile set 143. In the description that follows, only the first three of the five possible basal rate profiles are used. The operator may view basal rate profile information not shown in active window 106 by using scroll bar 176.

By default, the first depicted profile is designated as active by software 17. As such, active icon 172 is shown in association with thumbnail image 166A instead of activate button 174. The operator may select other available profiles to be made active by selecting the activate button 174 associated with the desired profile. As is also shown in FIG. 6, when a configuration file is opened or uploaded and active window 106 is populated with basal rate profile information, basal rate and bolus button 122 is automatically activated, causing the display of dropdown menu 178 in navigation menu 104. Dropdown menu 178 is also displayed upon opening or uploading a profile set or individual profile. Dropdown menu 178 includes a basal rate profile button 180 (which is depicted as active), a temporary basal rate button 182, and a bolus button 184. Finally, active window 106 further includes a status bar 186 which indicates the status of the currently active configuration file 141. Here, the status is unchanged.

The basal rate profiles associated with thumbnail images 166A-C may be modified in the manner described in co-pending patent applications entitled "USER INTERFACE FOR MANIPULATING GROUPS OF DATA REPRESENTATIONS OF A GRAPHICAL DISPLAY,"Ser. No. 12/205,582 and "INSULIN PUMP CONFIGURATION PROGRAMMING INVALID SETTINGS NOTIFICATION AND CORRECTION,"Ser. No. 12/205,587 the entire contents of which are hereby expressly incorporated herein by reference. Also, it should be understood that although portions of this description refer to hourly basal rate profiles, basal rate profiles may include basal rates that cover more or less than a one hour time period. Indeed, the time periods covered by basal rates in a profile need not be equal. The concepts of the present disclosure are not limited by the duration of an individual basal rate, and the references to hourly basal rates are only exemplary.

Figure 7:
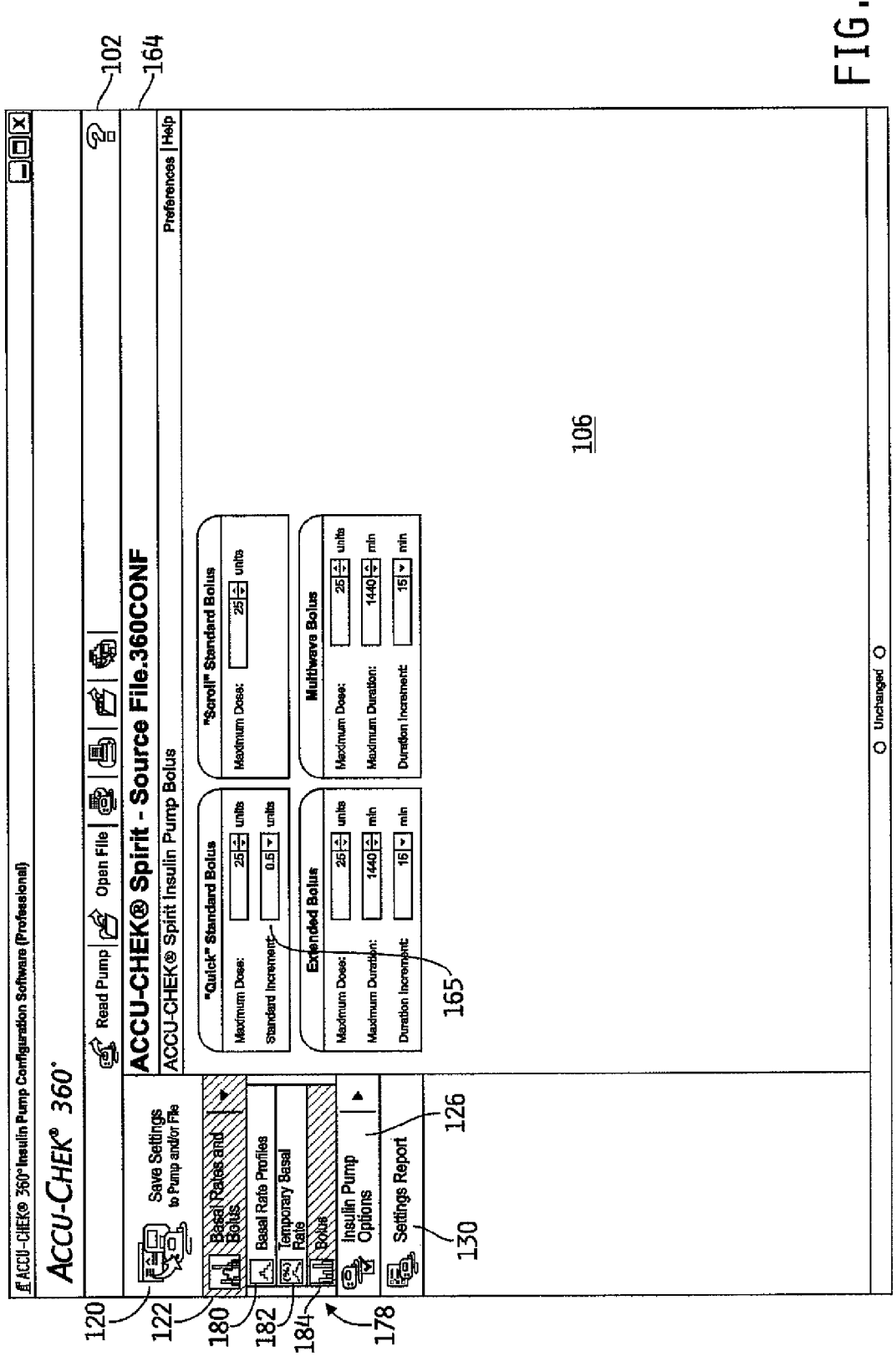
FIG. 7 is a screenshot depicting settings for bolus parameters.

As indicated above, configuration files include information other than basal rate profiles. For example, by activating bolus button 184, the operator has access to various bolus dose settings as shown in FIG. 7, all of which are known to persons skilled in the art. For purposes of the present description, it should be noted that the standard increment for "Quick" Standard Bolus 165 is set to 0.5. This is the amount of bolus insulin to be included in a bolus injection to compensate for carbohydrate consumption each time the user depresses up key 38. This bolus increment is an important pump parameter because inappropriately large bolus injections may cause the user to lose consciousness, which can be life threatening under a variety of circumstances (such as driving).

Figure 8:
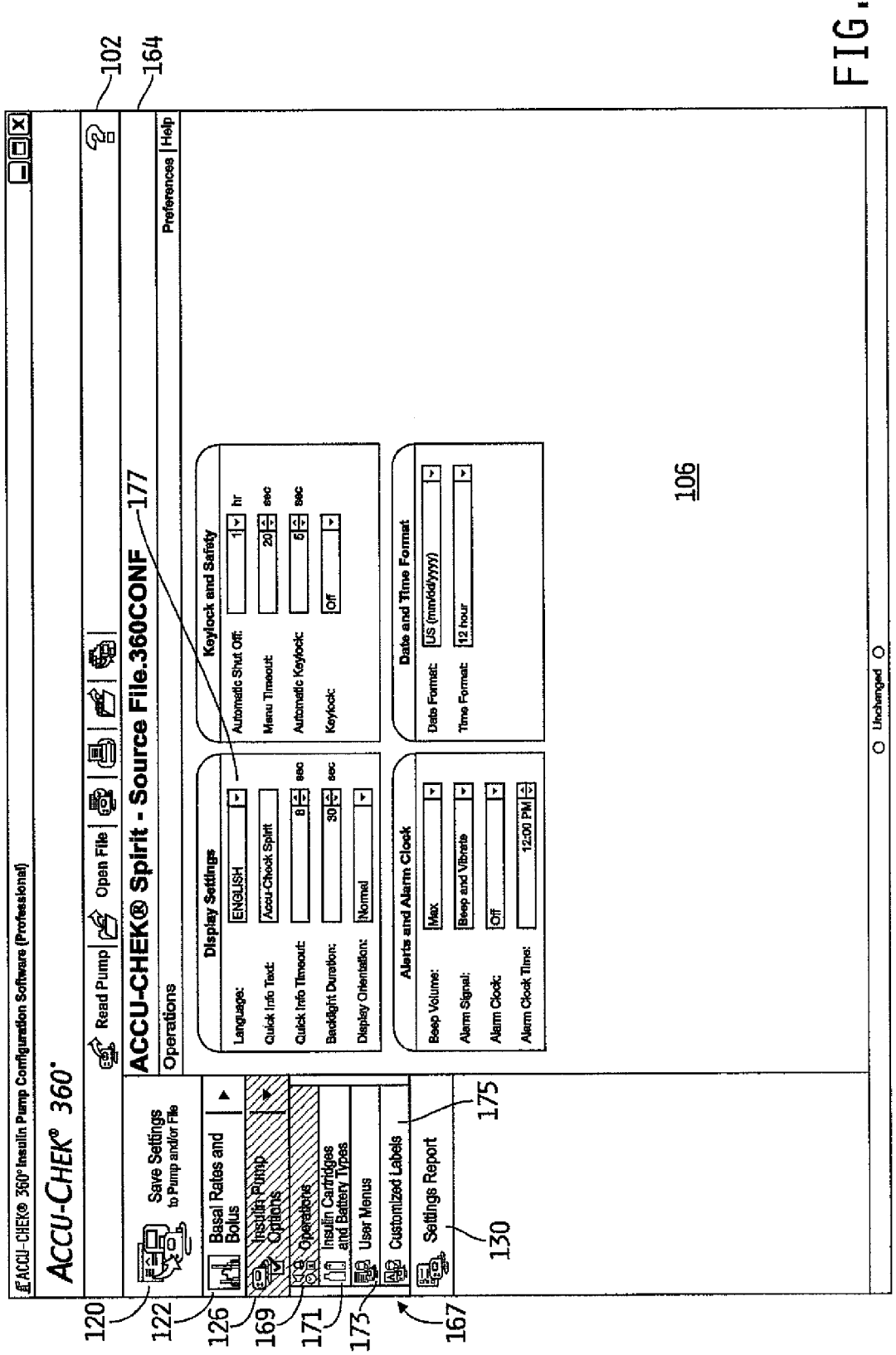
FIG. 8 is a screenshot depicting settings for various pump operations.

FIG. 8 depicts the various parameter settings accessible by activating insulin pump options button 126, which causes the display of dropdown menu 167, including operations button 169, cartridges and battery button 171, user menus button 173, and customized labels button 175. Activation of any of buttons 169, 171, 173, and 175 provide parameter settings options in active window 106. FIG. 8 depicts the parameter options displayed upon activation of operations button 169. For purposes of the present description, it should be noted that the language option 177 is set to English.

Figure 9:
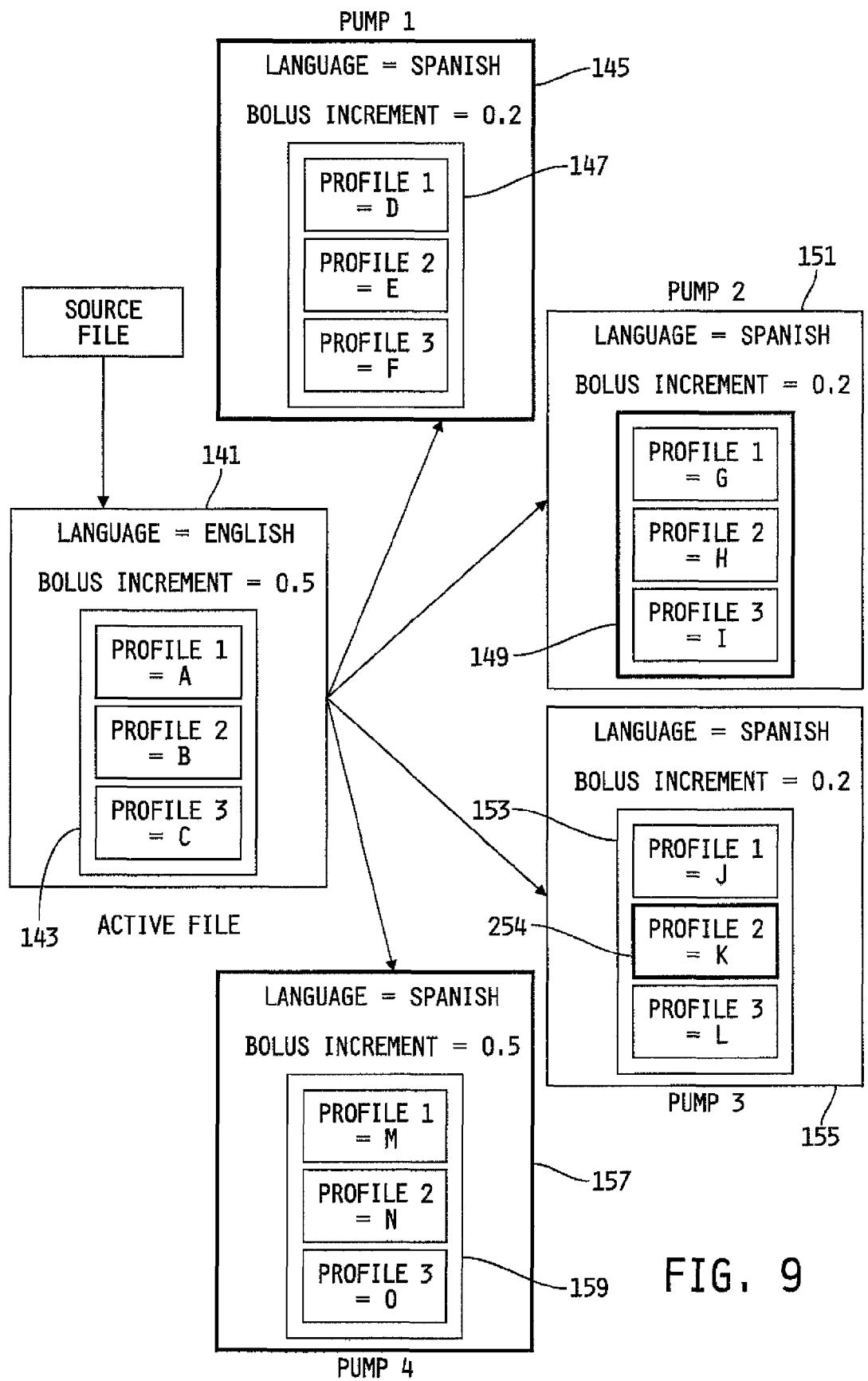
FIG. 9 is a conceptual diagram of various pump programming operations using an active configuration file.

At this point in the illustrative example, an entire configuration file 141 (i.e., Source File.360CONF) has been loaded by software 17 as the active file. To illustrate the principles of the present disclosure, assume that an operator (such as a health care provider) has loaded configuration file 141 for the purpose of programming four separate insulin pumps. FIG. 9 is a conceptual drawing illustrating the programming operations described in the remainder of this description. Configuration file 141 is depicted as the active file, obtained from a source file in the manner described above. Configuration file 141 includes, among other things, settings for language and bolus increment, as well as profile set 143, including individual basal rate profiles A-C (corresponding to thumbnail images 166A-C of FIG. 6). The language is English and the bolus increment is 0.5. Configuration file 141 will first be described as replacing configuration file 145 currently residing on pump 1, which includes a language parameter setting of Spanish, a bolus increment setting of 0.2, and a profile set 147 including three individual profiles D-F with hourly basal rates that differ from the hourly basal rates of profiles A-C of configuration file 141. Next, profile set 143 of configuration file 141 will be described as replacing profile set 149 of configuration file 151 currently residing on pump 2. Then, individual profile 2 of configuration file 141 will be described as replacing profile 2 of profile set 153 of configuration file 155 currently loaded on pump 3. Finally, to illustrate one kind of oversight the operator may make when replacing an entire configuration file instead of just a profile set or a single profile, configuration file 141 will be described as replacing configuration file 157 (instead of just profile set 159) currently residing on pump 4.

Figure 10:
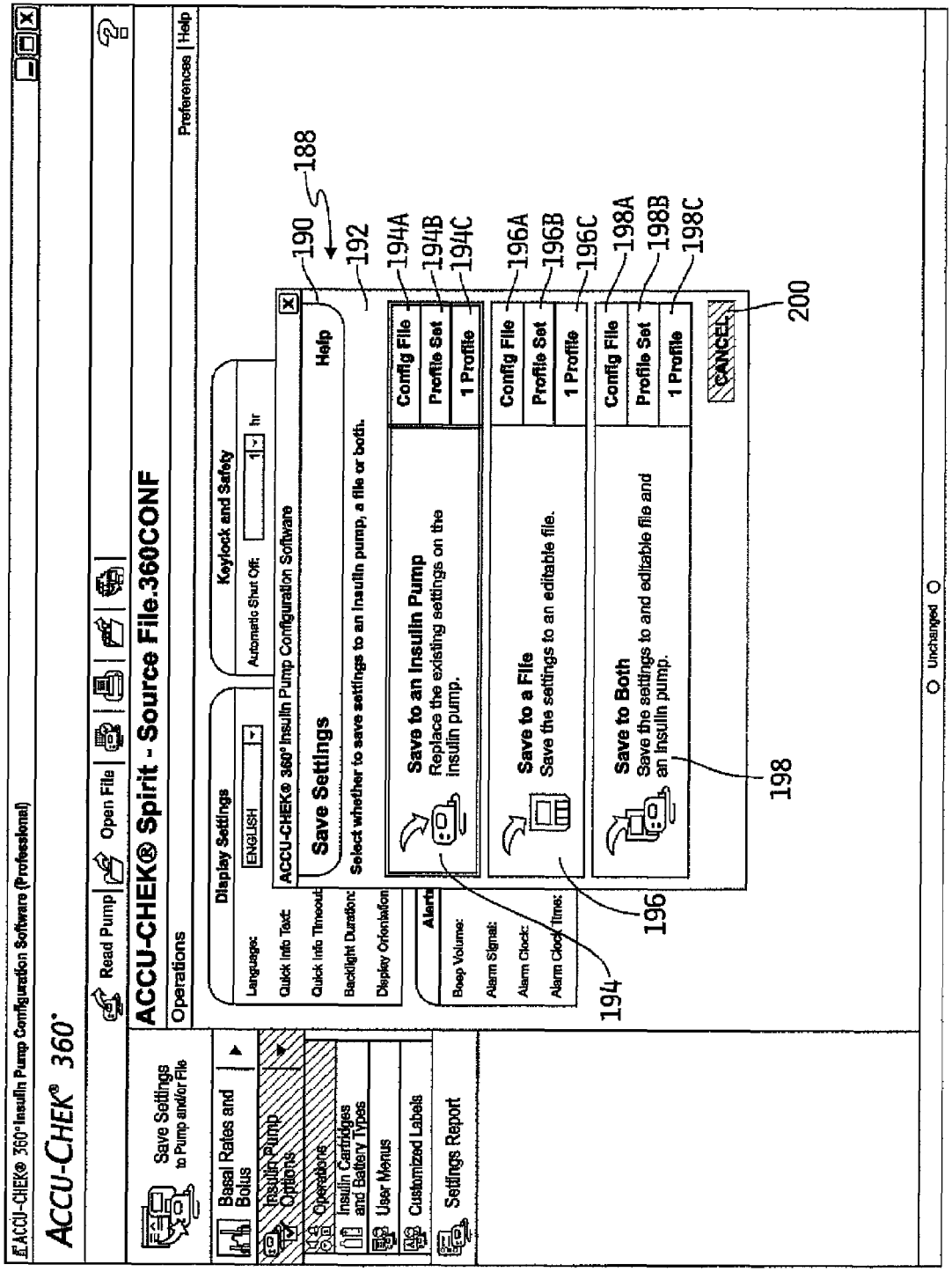
FIG. 10 is a screenshot including a save settings dialog box.

Referring back to FIG. 8, when the operator activates save settings button 120 as the first step in replacing configuration file 145 currently residing on pump 1 with active configuration file 141, the operator is presented with the screen of FIG. 10 which includes pop-up save settings dialog box 188. Dialog box 188 includes a title bar 190, a message area 192, a save to pump area 194 with a configuration file button 194A, a profile set button 194B, and a single profile button 194C, a save to file area 196 including a configuration file button 196A, a profile set button 196B, and a single profile button 196C, a save to both area 198 including a configuration file button 198A, a profile set button 198B, and a single profile button 198C, and a cancel button 200. To replace configuration file 145 with active configuration file 141, the operator activates save to pump configuration file button 194A. Although not depicted in the figures, it should be understood that any of the save to pump functions described herein may be readily adapted to guide the operator through steps for saving information to multiple insulin pumps in a single workflow.

Figure 11:
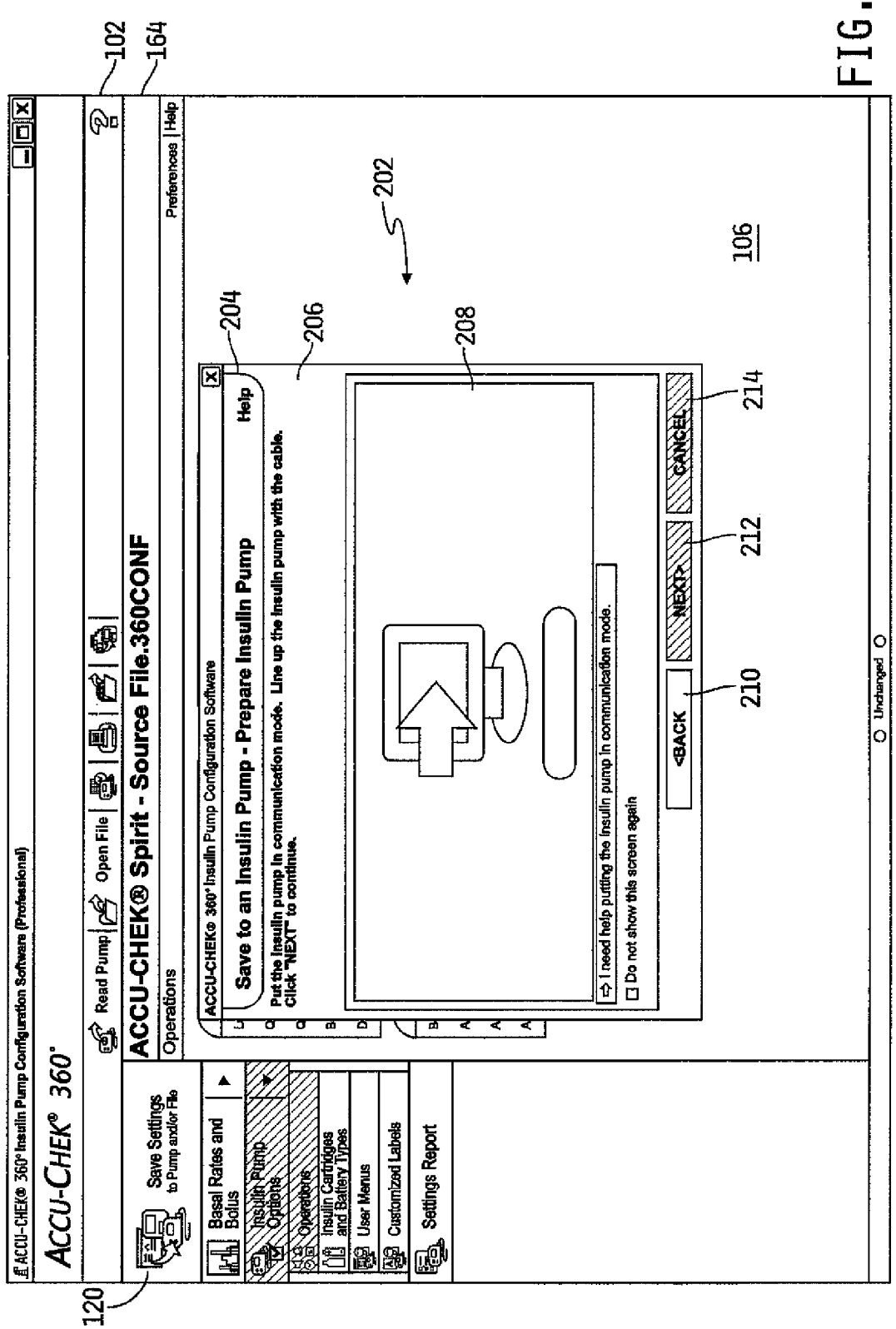
FIG. 11 is a screenshot including a communication status dialog box.

When button 194A is activated, FIG. 11 is displayed, including communication status dialog box 202. Dialog box 202 includes title bar 204, message area 206, status window 208, back button 210, next button 212, and cancel button 214. Title bar 204 indicates that a save to pump operation is being performed. Message area 206 provides instructions to the operator for performing the operation, and status window 208 provides graphical and/or textual information about the operation. As shown in the figure, the operator is provided instructions in message area 206 for preparing pump 1 for communications with computing device 12. A variety of different communication technologies may be employed to facilitate this communication. In this example, the operator is instructed to place pump 1 in communication mode and align pump 1 with dongle 26 for IR communications with computing device 12. When pump 1 is prepared for communications, the operator activates next button 212.

Figure 12:
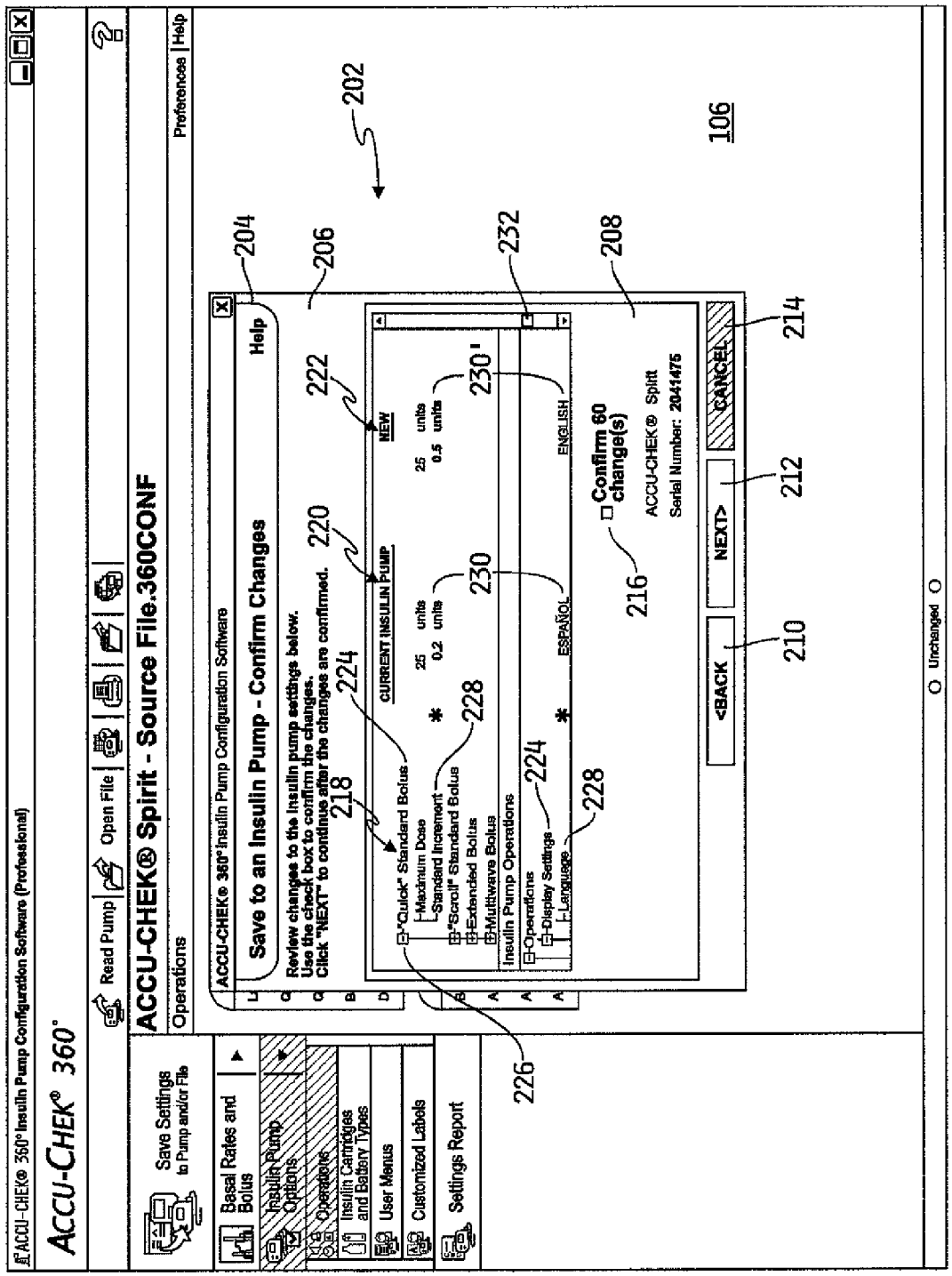
FIGS. 12 and 13 are screenshots wherein the communication status dialog box of FIG. 11 includes a comparison of information to be programmed and a confirm change box.

Before downloading configuration file 141 to pump 1, software 17 displays confirmation instructions in communications status dialog box 202 as depicted in FIG. 11. As shown, message area 206 instructs the operator to review the changes that are about to be made to the pump being programmed, and to check the confirm changes box 216 to approve the changes. Status window 208 includes a configuration file tree structure 218, a current pump information column 220, and a new information column 222. Configuration file tree structure 218 includes a plurality of different parameter titles 224 accompanied by expander icons 226 that, when activated, cause the display of parameter names 228 associated with the parameter title 224. Current pump information column 220 includes data fields 230 corresponding to each displayed parameter name 228. Data fields 230 include the status or value of the named parameter as they exist in the pump about to be programmed (here, pump 1). New information column 222 similarly includes data fields 230' that reflect the data in the active configuration file 141 about to replace the existing configuration file 145 of pump 1. As also shown in FIG. 12, parameters that will change upon programming pump 1 are highlighted. The operator can scroll through the information presented in status window 208 using scrollbar 232.

Although not apparent from FIG. 12, software 17 is configured to automatically position the information in status window 208 such that the most critical information changes may be viewed without having to use scrollbar 232. When more information changes are present than can be simultaneously displayed in the viewable area of status window 208, software 17 is configured to prioritize the changes and automatically position the information such that the most critical information (i.e., changes to parameters most likely to affect the safe operation of pump 24 or the health of the user) is shown in the viewable area of status window 208. Here, the change in bolus increment is shown as the most critical parameter change. Window 208 also shows the change in language from Spanish to English. As indicated above with reference to FIG. 9, profile set 147 currently present on pump 1 is also being replaced by profile set 143 of configuration file 141. The operator must use scrollbar 232 to view these basal rate profile changes.

Figure 13:
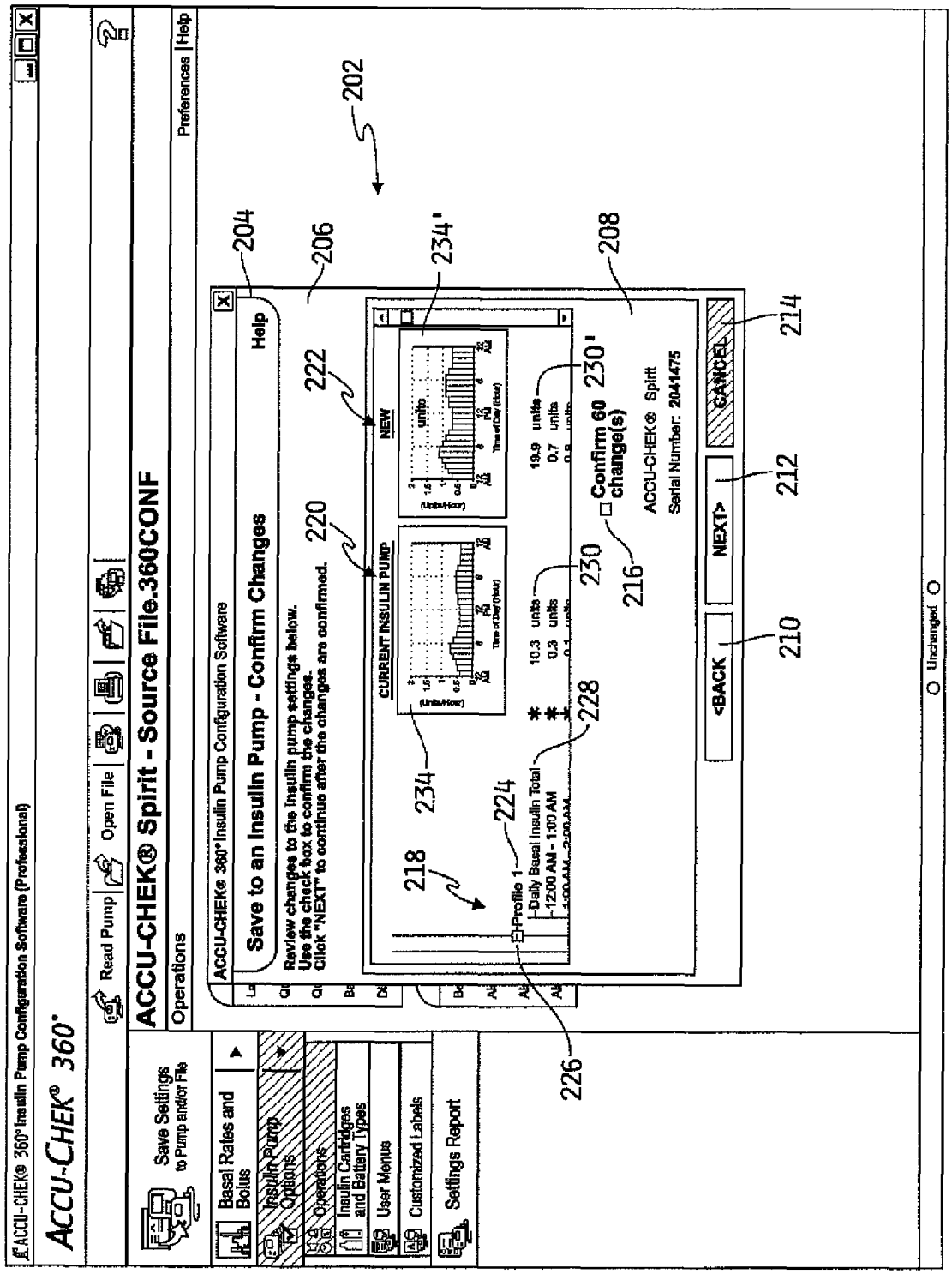

As shown in FIG. 13, when the operator uses scrollbar 232 to scroll upwardly, the operator may review changes about to be made to profile set 147. In this view, new information column 222 includes a thumbnail image 234' that corresponds to thumbnail image 166A of FIG. 6 (i.e., profile 1 of profile set 143). Current pump information column 220 includes a thumbnail image 234 that graphically depicts the data associated with basal rate profile 1 of profile set 147 on pump 1.

Figure 14:
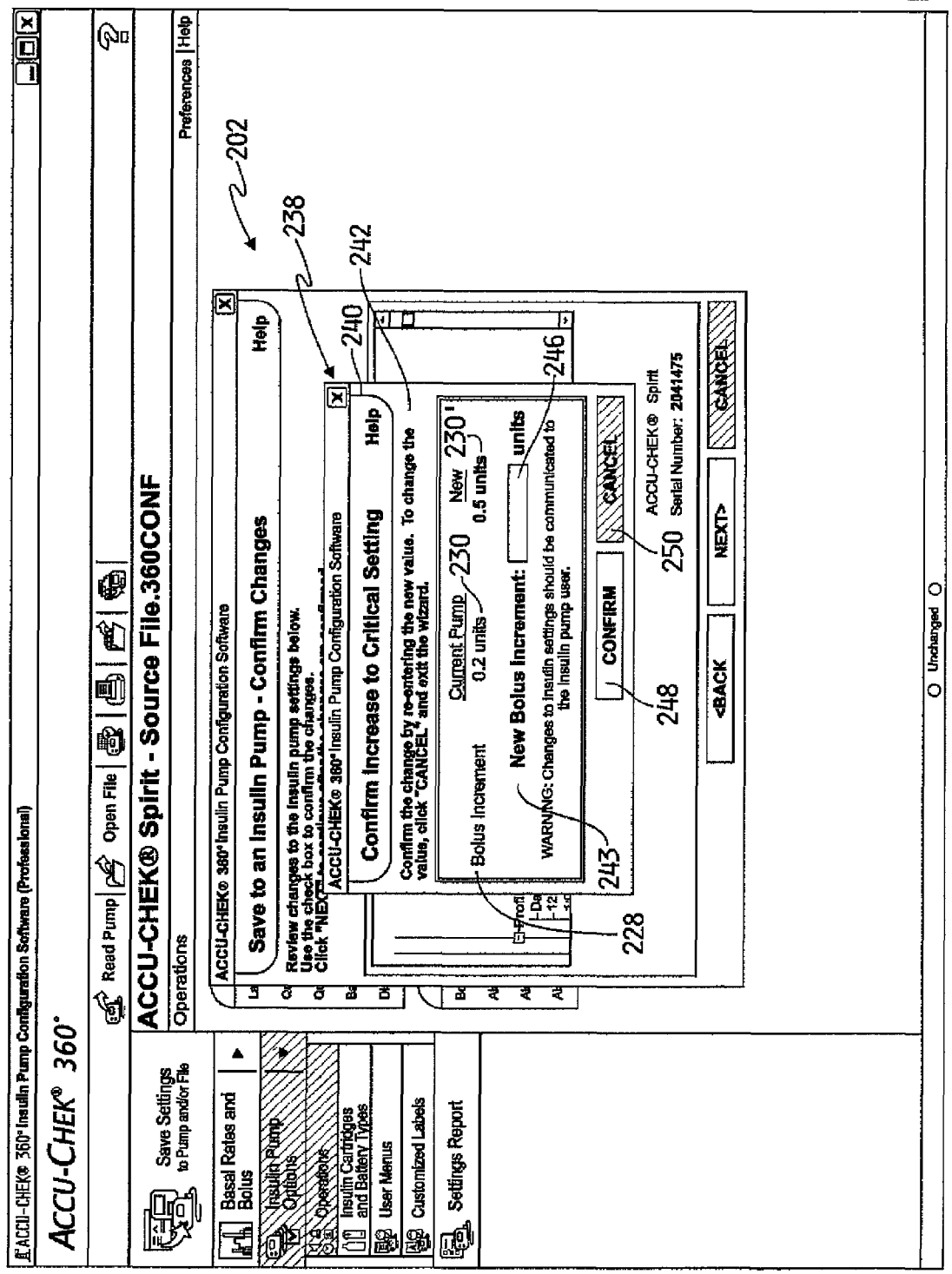
FIG. 14 is a screenshot including a critical change confirmation box for a bolus increment change.

After the operator reviews the changes about to be made to configuration file 145 by comparing the information in the highlighted data fields 230, 230', the operator must check the confirm changes box 216 and activate next button 212. As shown in FIG. 14, this causes software 17 to generate critical change confirmation box 238 which functions as a second verification level before making a change to a pump parameter that may have a serious adverse affect on the user's health. Here, the subject of critical change confirmation box 238 is an increase in the bolus increment. Under delivery of insulin may result in hyperglycemia (high blood glucose levels), which may increase the risk of infection and, if persistent for long periods, may cause damage to the retinas and kidneys, and nerve damage. Over delivery of insulin, on the other hand, may lead immediately to hypoglycemia, which can result in seizures, unconsciousness, and other highly undesirable manifestations of low blood glucose levels.

As shown, critical change confirmation box 238 includes a title bar 240, a message area 242 that instructs the user to re-enter the new data for the parameter about to be changed, a data window 243 showing the parameter name 228, the current pump data 230, and the new data 230', and including a data field 246 for re-entry of the new data. Box 238 also includes a confirm button 248 and a cancel button 250. Instead of requiring the operator to simply check a confirm changes box, which the operator may do without carefully reviewing the parameters being changed, critical change confirmation box 238 requires the operator to type the new data value exactly as it is shown in data field 230' and activate confirm button 248 to approve the change. In this example, the operator types 0.5 into data field 246.

In one embodiment of the present disclosure, activation of cancel button 250 returns the operator to the save settings dialog box 188 of FIG. 10. In an alternate embodiment, only the parameter that is the subject of the current critical change confirmation box 238 is not written to pump 24, but the programming workflow described herein continues.

Figure 15:
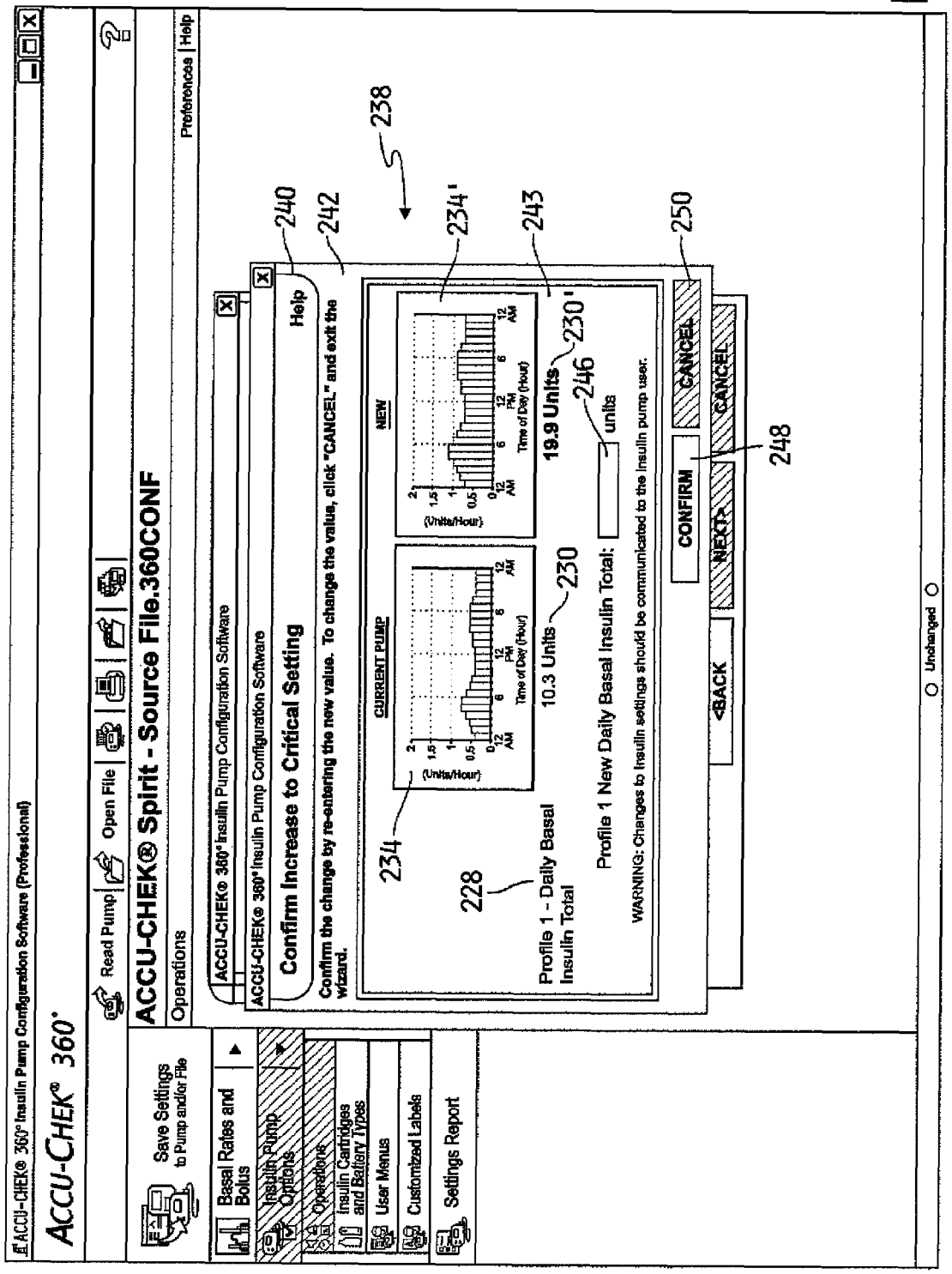
FIGS. 15 through 17 are screenshots including critical change confirmation boxes for basal profile changes.
Figure 16:
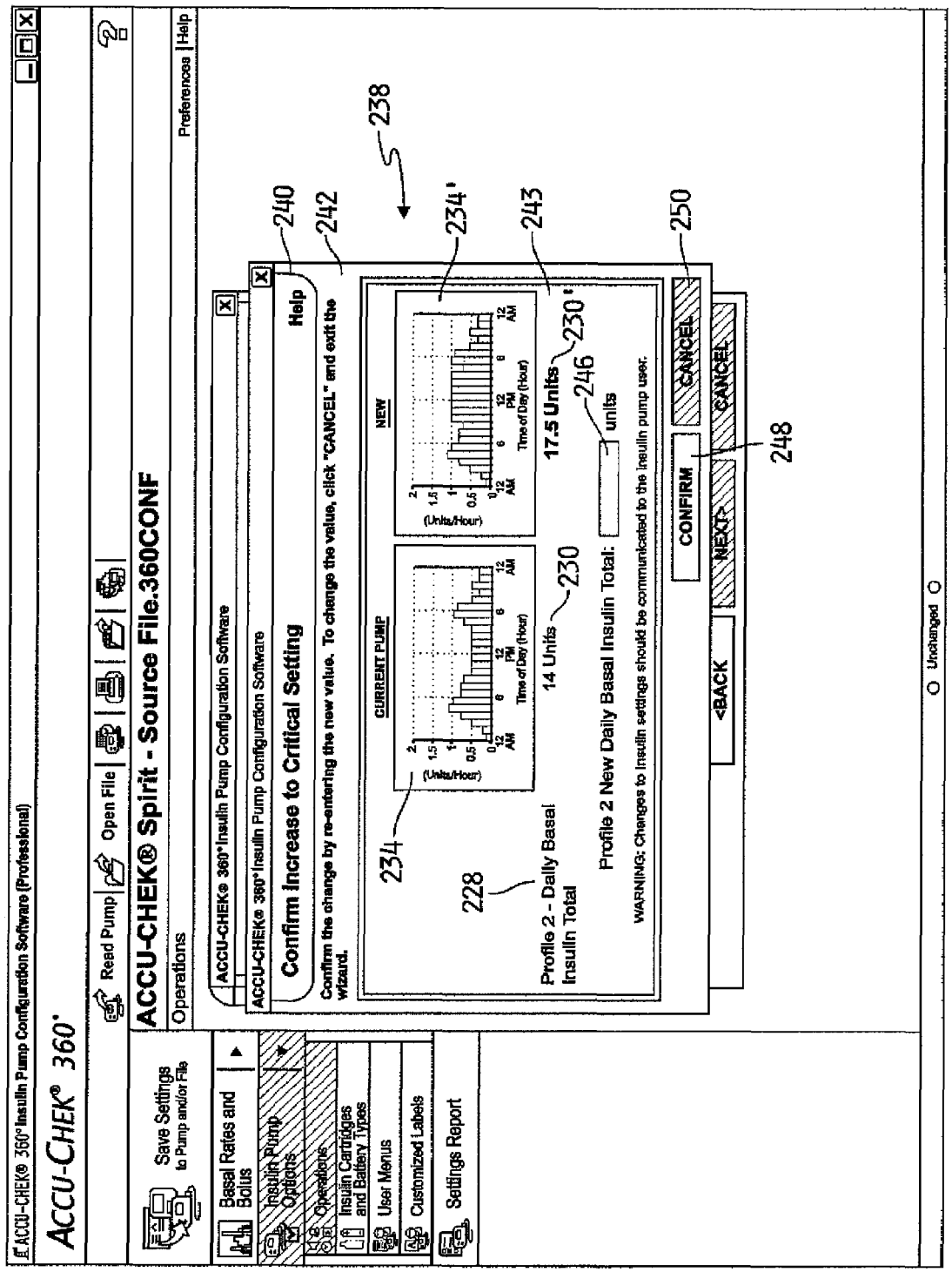
Figure 17:
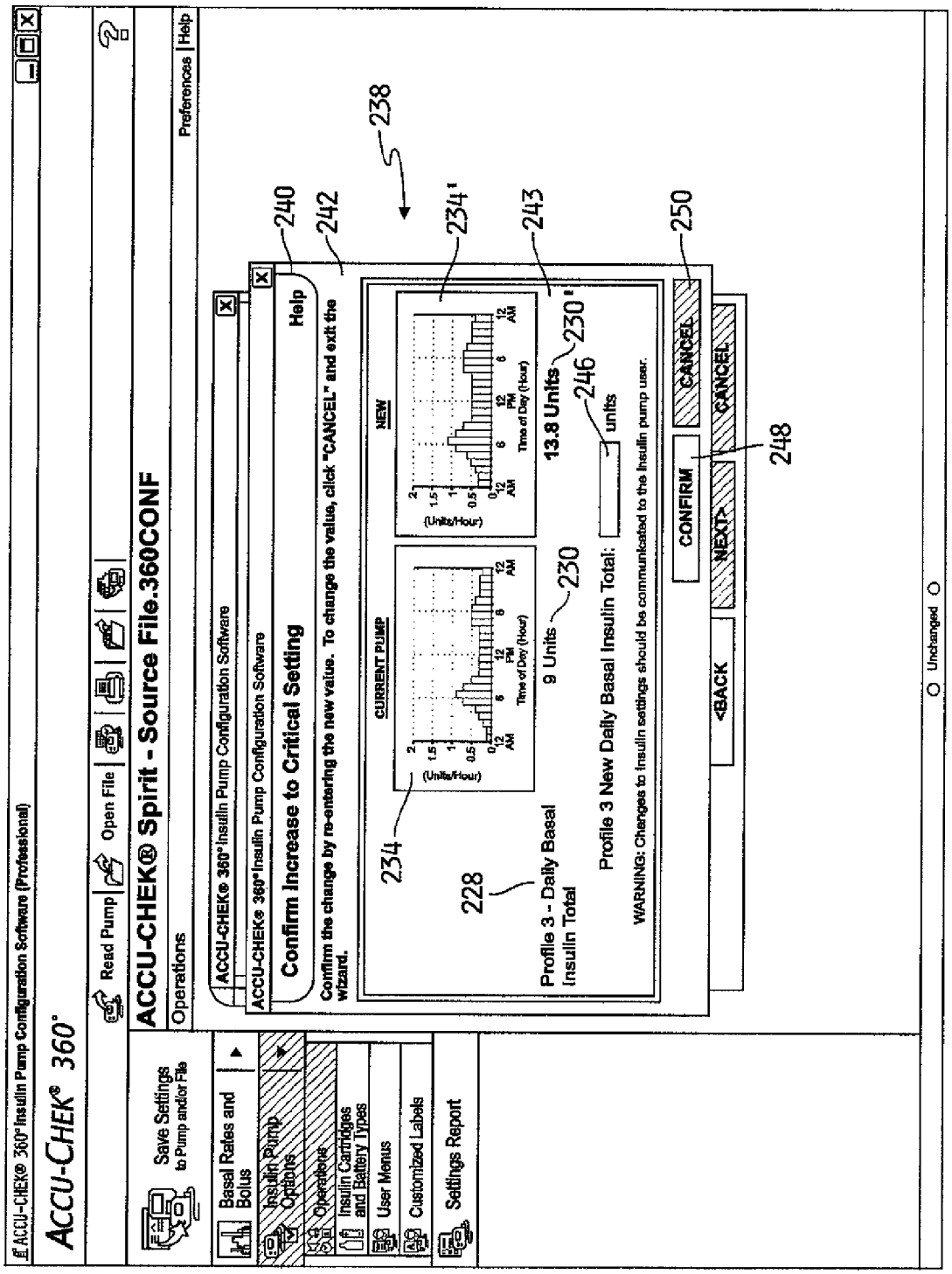

After the operator activates confirm button 248 in FIG. 14, a new critical change confirmation box 238 is displayed as shown in FIG. 15. In FIG. 15, data window 243 includes information, including thumbnail images 234, 234' reflecting the change about to be made to the daily basal insulin total associated with profile 1 of profile set 147. Like an increase in bolus increment, an increase in daily basal insulin total may have a serious adverse affect if accidentally programmed into pump 1. Accordingly, the operator is required to re-enter the new data (i.e., 19.9 units) exactly into data field 246, then activate confirm button 248 to proceed. After entering the new data value and activating confirm button 248, the operator is presented with another critical change confirmation box 238 as shown in FIG. 16. The critical change confirmation box 238 of FIG. 16 includes information similar to that shown in FIG. 15, but reflects the changes about to be made to the daily basal insulin total associated with profile 2 of profile set 147. Again, the operator is required to re-enter the new data (i.e., 17.5 units) exactly into data field 246, then activate confirm button 248 to proceed. After entering the new data value and activating confirm button 248, the operator is presented with yet another critical change confirmation box 238 as shown in FIG. 17. Once again, to change the daily basal insulin total associated with profile 3 of profile set 147, the operator must re-enter the new data (i.e., 13.8 units) exactly into data field 246, then activate confirm button 248 to proceed. Additional critical change confirmation boxes 238 would be presented to the operator if insulin increases for profiles 4 and 5 were to be programmed into profile set 147.

Figure 18:
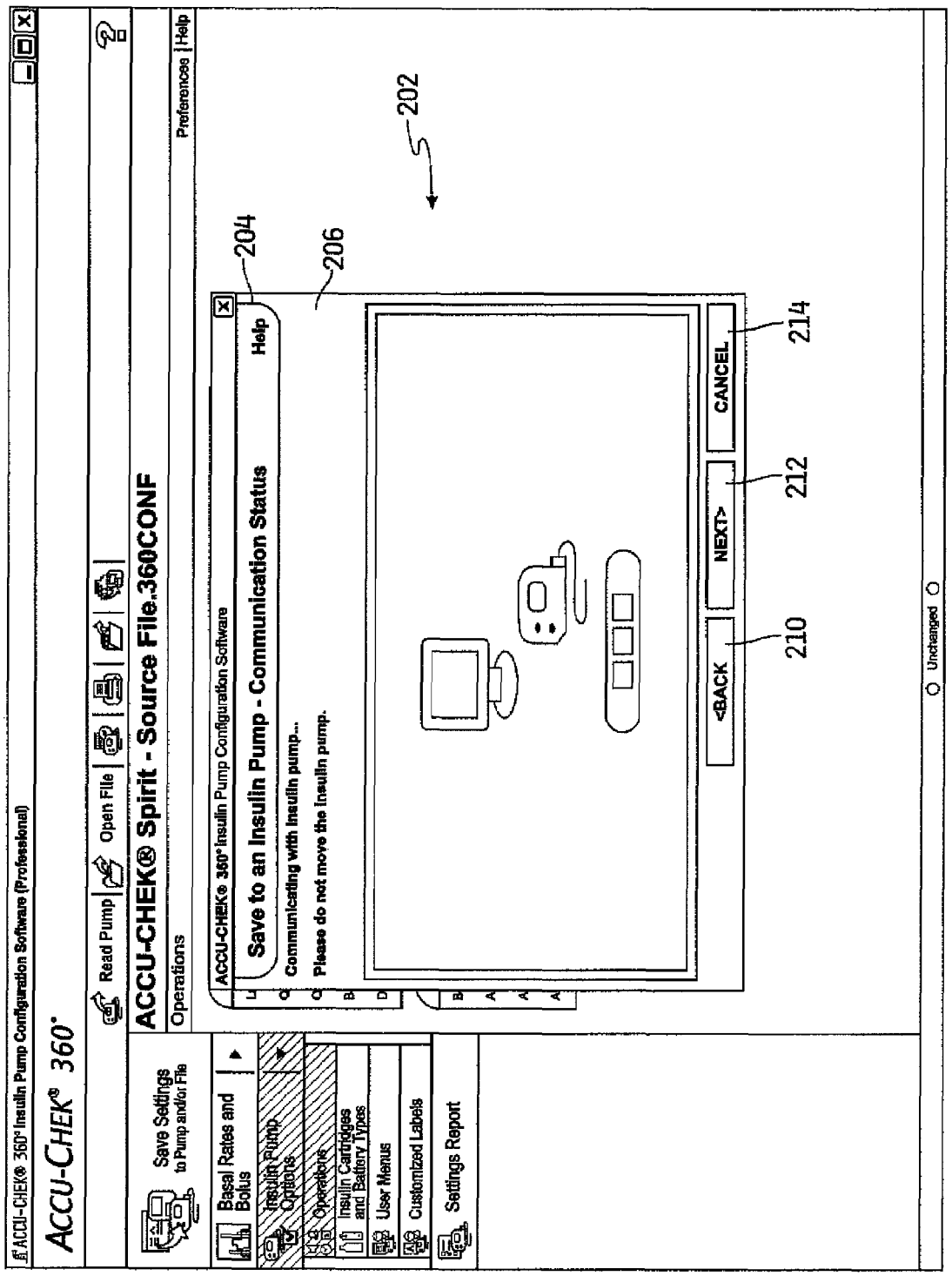
FIGS. 18 and 19 are screenshots similar to that of FIG. 11.
Figure 19:
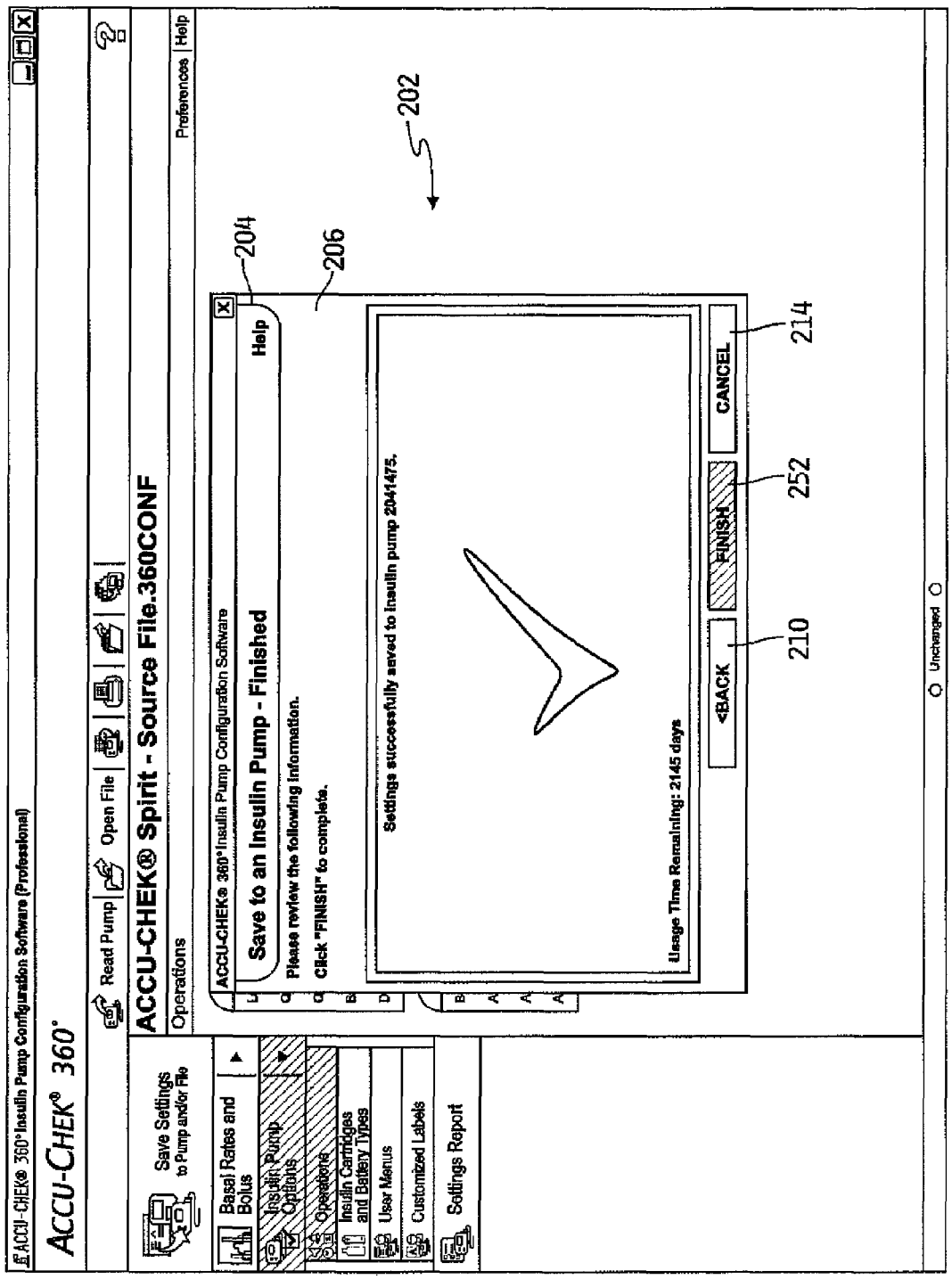
Figure 20:
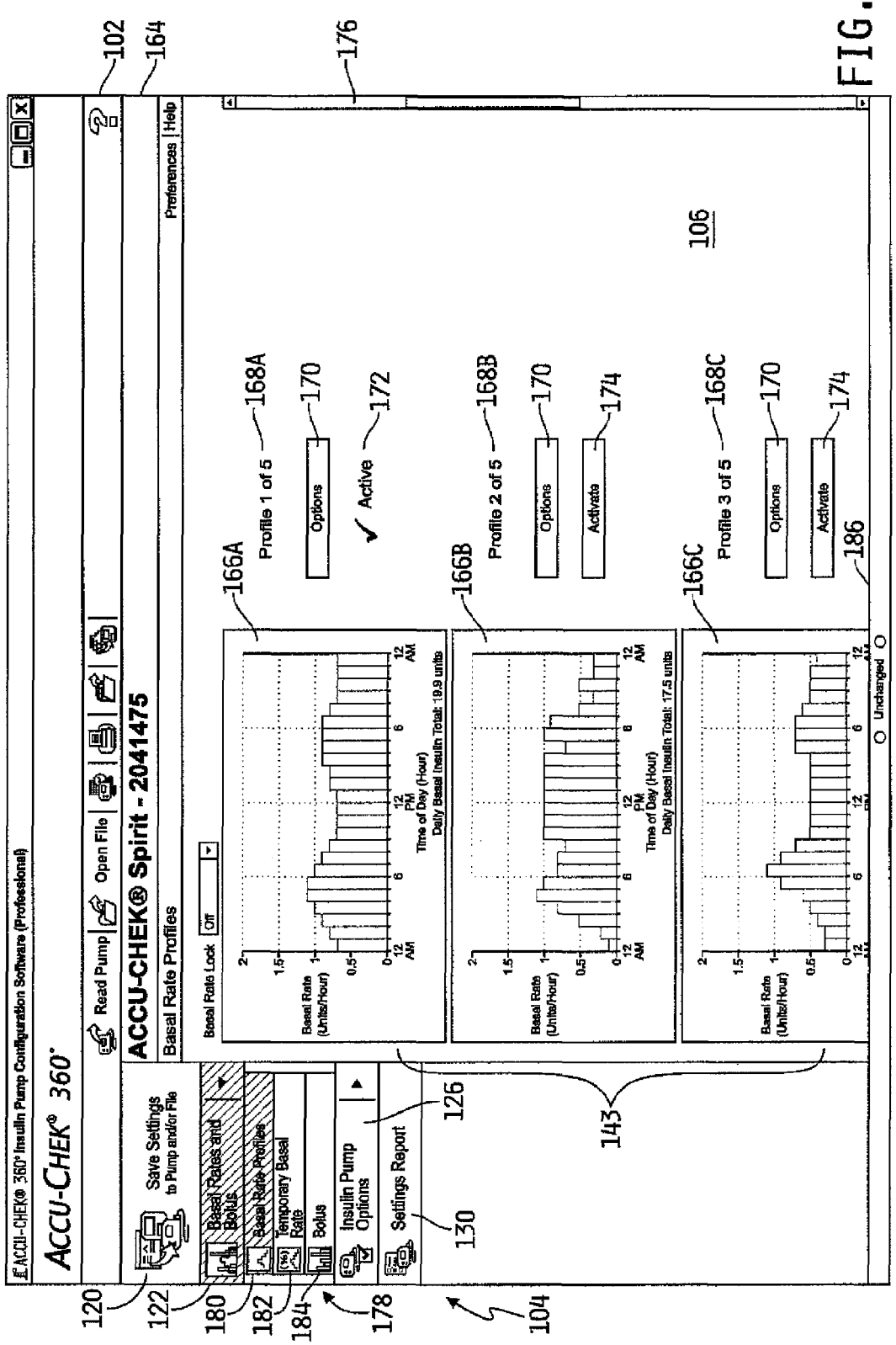
FIG. 20 is a screenshot similar to that of FIG. 6.

Finally, after re-entering the new data (i.e., 13.8 units) into data field 246 of FIG. 17 and activating confirm button 248, communication status dialog box 202 of FIG. 18 is displayed to indicate that configuration file 141 is being programmed into the memory of pump 1. When the programming is complete, communication status dialog box 202 of FIG. 19 is displayed to indicate successful programming. When the operator activates the finish button 252 of dialog box 202, active window 106 of FIG. 20 is displayed. FIG. 20 is similar to FIG. 6, except that the information displayed reflects the newly programmed configuration file present on pump 1 (the now current active file). Accordingly, the serial number for pump 1 is displayed in title bar 164. Otherwise, the two figures are identical as the information (e.g., thumbnail images 166A-C) of the newly programmed configuration file is identical to that of previously active file 141.

As described above, to replace configuration file 145 of pump 1 with configuration file 141, the operator is required to check confirm box 216 and activate next button 212 (FIG. 12), and re-enter data into data fields 246 (followed by activating confirm button 248) for four critical data changes (i.e., bolus increment (FIG. 14), daily basal insulin total for profile 1 (FIG. 15), daily basal insulin total for profile 2 (FIG. 16), and daily basal insulin total for profile 3 (FIG. 17)).

In the next example programming session, the operator is described as replacing profile set 149 of pump 2 (see FIG. 9) with profile set 143 of configuration file 141. As shown in FIG. 9, pump 2 is currently programmed to use Spanish and provide a bolus increment of 0.2. These parameters are to remain unchanged by the programming. One method for accomplishing a change to only profile set 149 is to activate configuration file 141 in the manner described above, and change the setting for the standard increment for "Quick" Standard Bolus 165 (FIG. 7) from 0.5 to 0.2 and the setting for the language option 177 (FIG. 8) from English to Spanish. After these changes (and any other differences in general configuration data) are complete, the operator may save the modified version of configuration file 141 to pump 2 using save to pump configuration file button 194A (FIG. 10) as described above. This approach, of course, requires the operator to determine the differences in general configuration data between configuration file 141 and configuration file 151, which may be a time consuming, error-prone task. Alternatively, the operator may activate configuration file 141 in the manner described above, and activate save to pump profile set button 194B of FIG. 10. As software 17 will not attempt to program information on pump 2 other than profile set 149 when button 194B is activated, the operator need not determine what other differences (if any) exist between active configuration file 141 and configuration file 151 currently present on pump 2. After the operator activates button 194B of FIG. 10, and next button 212 of communication status dialog box 202 (FIG. 11), communication status dialog box 202 is displayed in active window 106 as shown in FIG. 21.

Figure 21:
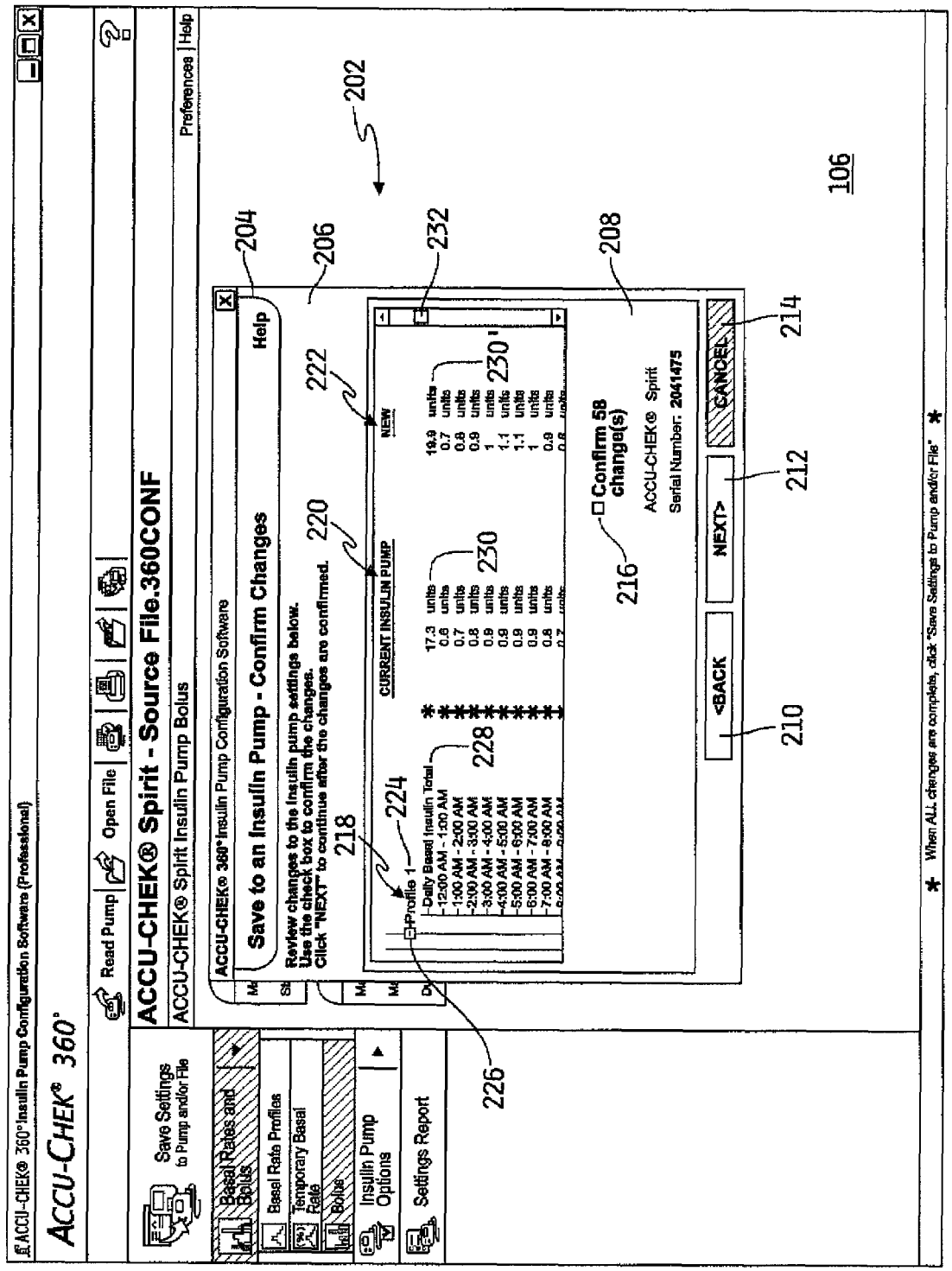
FIG. 21 is a screenshot similar to that of FIG. 11.

The screen depicted in FIG. 21 is similar to the screen depicted in FIGS. 12 and 13. As shown, message area 206 instructs the operator to review the changes that are about to be made to the pump being programmed, and to check the confirm changes box 216 to approve the changes. Configuration file tree structure 218, current pump information column 220, and new information column 222 are automatically scrolled as described above to display (with highlighting) changes to be made to profile 1. The operator can scroll through the information presented in status window 208 using scrollbar 232 to review changes to be made to profiles 2 and 3.

Figure 22:
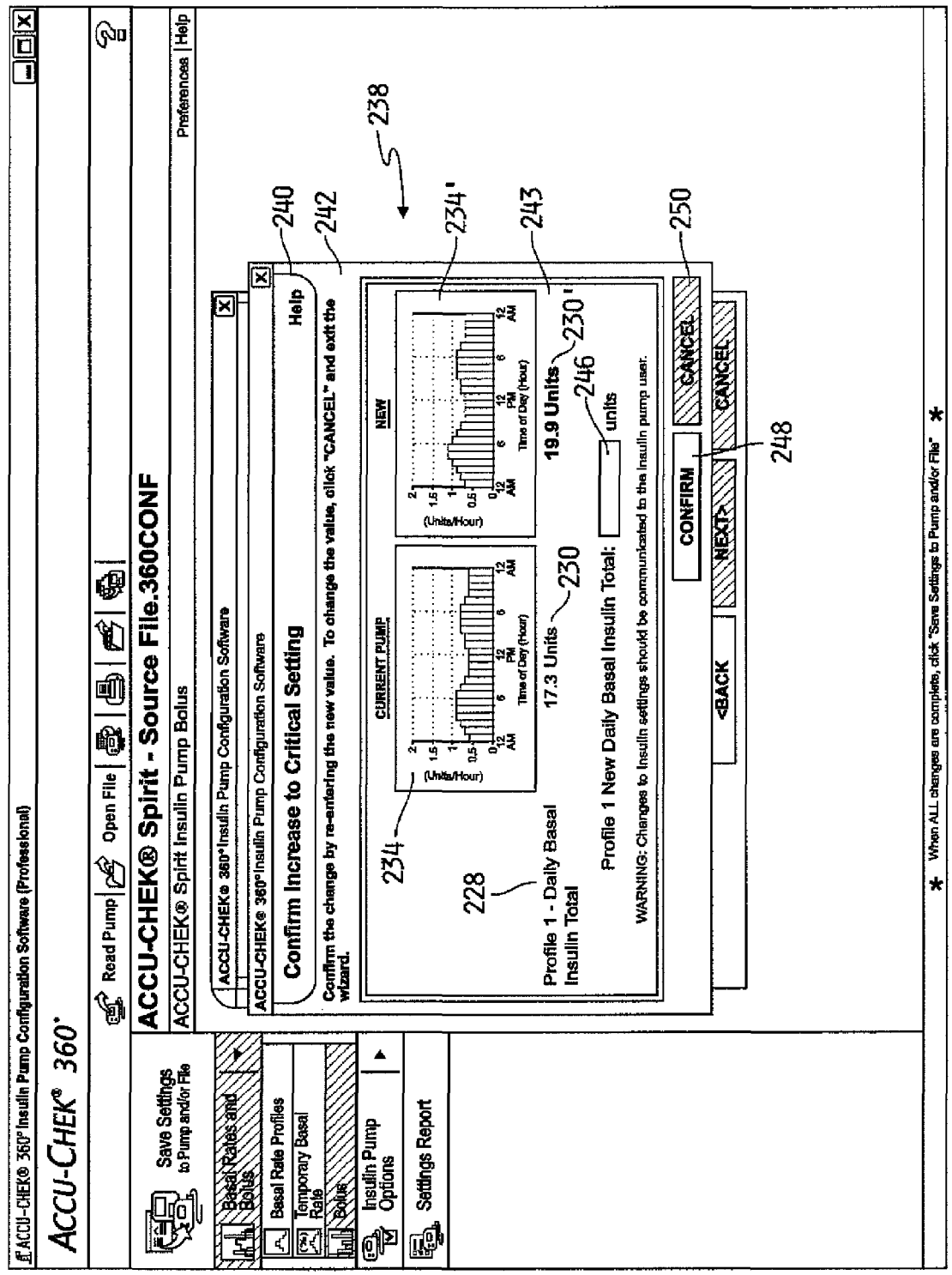
FIG. 22 is a screenshot similar to that of FIG. 15.

After the operator reviews the changes, checks confirm changes box 216, and activates next button 212, critical change confirmation box 238 is displayed as shown in FIG. 22. It should be noted that the confirmation step for changing the bolus increment did not occur in this example as the bolus increment of configuration file 141 is not being written to configuration file 151. Critical change confirmation box 238 is similar to that described above with reference to FIG. 15. It depicts changes about to be made to profile 1 of profile set 149. After the operator re-enters the new daily basal insulin total (i.e., 19.9 units) in data field 246 and activates confirm button 248, the operator is presented with screens corresponding to FIGS. 16 though 20 which guide the operator through critical data changes to profiles 2 and 3 and completion of the programming operation for pump 2.

An alternative approach to programming pump 2 with profile set 143 according to the teachings of the present disclosure is to simply retrieve profile 143 from the source file "Source File.360CONF" using open profile set button 138B or open file icon 110 of FIG. 4. Using open file dialog box 144 of FIG. 5, the operator may simply activate profile set 143 for programming pump 2. In this manner, the operator can avoid programming pump 2 with incorrect general configuration data by accidentally activating save to pump configuration file button 194A (FIG. 10) instead of save to pump profile set button 194B. When only a profile set is made active by software 17 (as opposed to an entire configuration file), configuration file buttons 194A, 196A, and 198A of save settings dialog box 188 are disabled. Once profile set 143 is made active and the operator activates save to pump profile set button 194B, the programming sequence is identical to that described above with reference to FIGS. 21 and 22.

In the next example programming session, the operator is described as replacing individual profile 2 of profile set 153 (hereinafter referred to as individual profile 254—see FIG. 9) on pump 3 with individual profile 2 of profile set 143. As shown in FIG. 9, pump 3 is currently programmed to use Spanish and provide a bolus increment of 0.2. Individual profiles 1 and 3 are depicted as having generalized values of J and L, respectively, which are different from the corresponding generalized values for profiles 1 and 3 of profile set 143. All of these currently programmed parameters are to remain unchanged by the programming. One method for accomplishing a change to only individual profile 254 is to activate configuration file 141 in the manner described above, and change the settings for bolus increment, language, profile 1 and profile 3 to match the settings currently present on pump 3. After these changes are complete, the operator may save the modified version of configuration file 141 to pump 3 using save to pump configuration file button 194A (FIG. 10) as described above. This approach, of course, requires the operator to determine the differences between configuration file 141 and configuration file 155 and make the necessary changes, which may be a time consuming, error-prone task.

Alternatively, the operator may activate configuration file 141 in the manner described above, and activate save to pump individual profile button 194C of FIG. 10. As software 17 will not attempt to program information on pump 3 other than individual profile 254 when button 194C is activated, the operator need not determine what other differences (if any) exist between active configuration file 141 and configuration file 155 currently present on pump 3. After the operator activates button 194C of FIG. 10, and next button 212 of communication status dialog box 202 (FIG. 11), communication status dialog box 202 is displayed in active window 106 as shown in FIG. 23.

Figure 23:
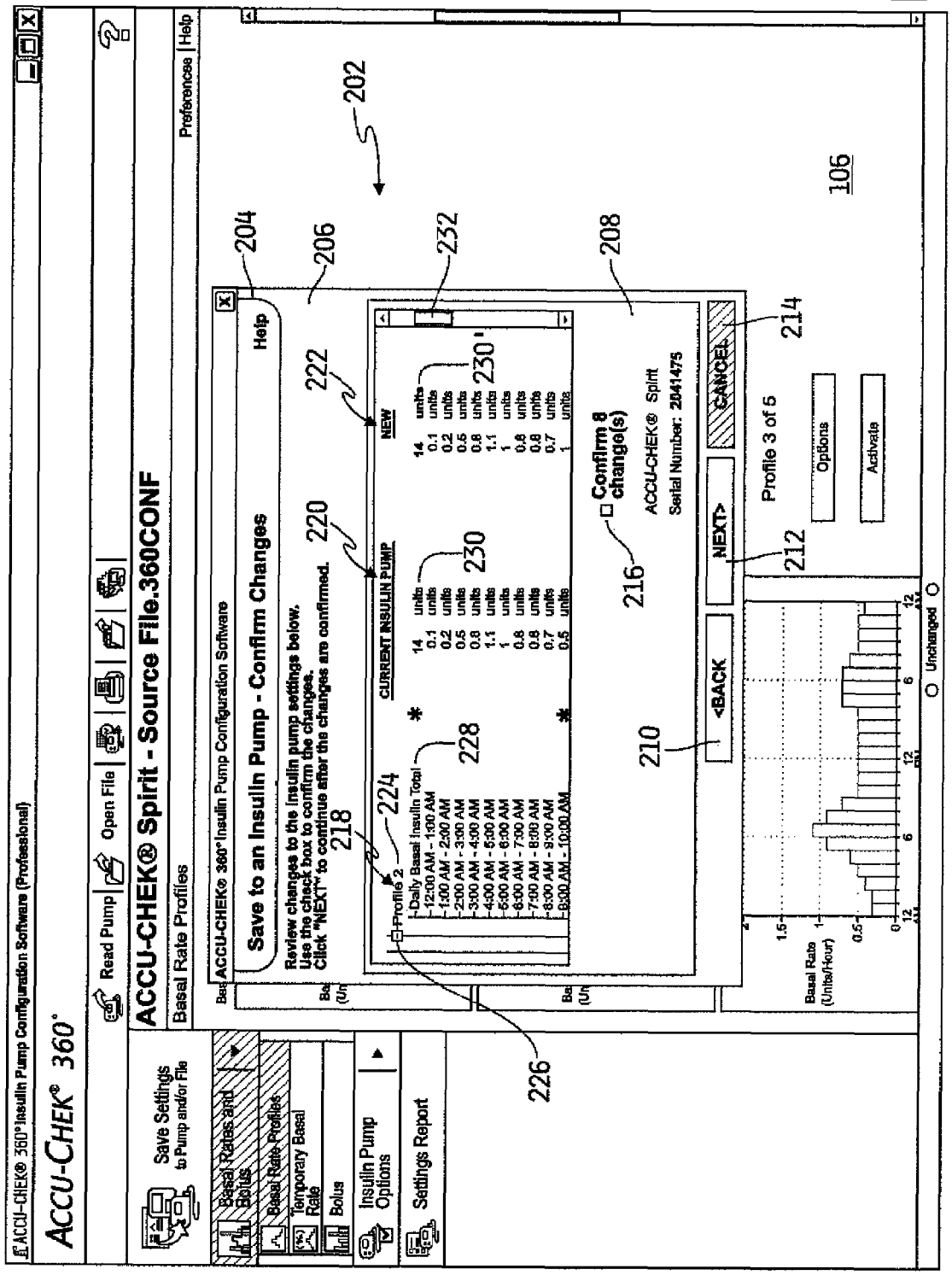
FIG. 23 is a screenshot similar to that of FIG. 11.
Figure 24:
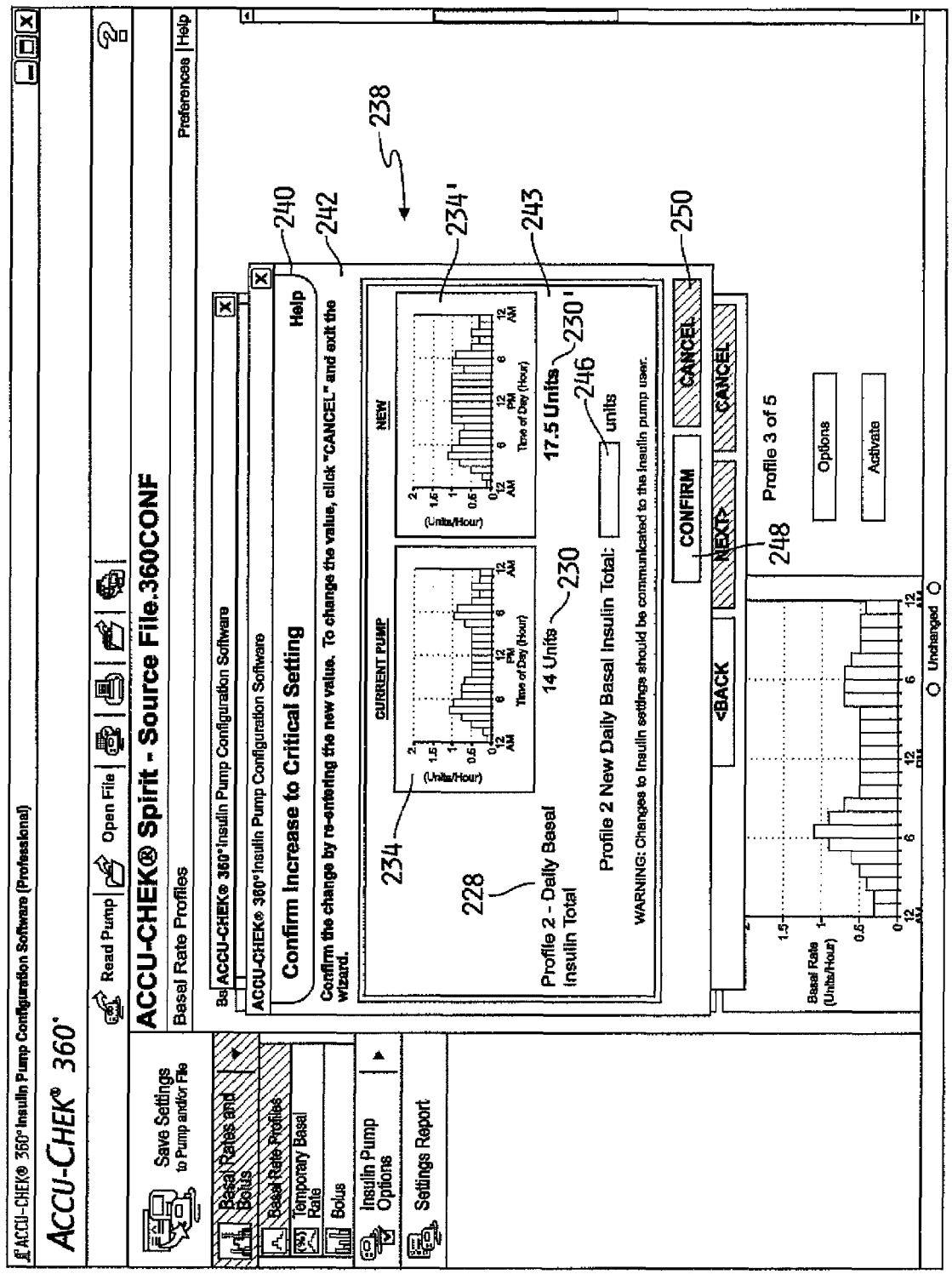
FIG. 24 is a screenshot similar to that of FIG. 16.

The screen depicted in FIG. 23 is similar to the screen depicted in FIGS. 12 and 13. Here, however, the only highlighted changes are those to be made to individual profile 254. After the operator reviews the changes, checks confirm changes box 216, and activates next button 212, critical change confirmation box 238 is displayed as shown in FIG. 24, which is similar to the display depicted in FIG. 16. This is the only critical change confirmation box 238 presented to the operator in this programming example as only individual profile 254 is being programmed. After the operator re-enters the new daily basal insulin total (i.e., 17.5 units) in data field 246 and activates confirm button 248, the operator is presented with screens corresponding to FIGS. 18 though 20 which complete the programming operation for pump 3.

An alternative approach to programming pump 3 with individual profile 2 of profile set 143 according to the teachings of the present disclosure is to simply retrieve individual profile 2 from the source file "Source File.360CONF" using open individual profile button 138C or open file icon 110 of FIG. 4. Using open file dialog box 144 of FIG. 5, the operator may simply activate individual profile 2 for programming pump 3. In this manner, the operator can avoid inadvertently attempting to program pump 3 with general configuration data or changes to other individual profiles by accidentally activating save to pump configuration file button 194A or save to pump profile set button 194B (FIG. 10) instead of save to pump individual profile button 194C. When an individual profile is made active by software 17 (as opposed to an entire configuration file or a profile set), configuration file buttons 194A, 196A, and 198A and profile set buttons 194B, 196B, and 198B of save settings dialog box 188 are disabled. Once individual profile 2 of profile set 143 is made active and the operator activates save to pump individual profile button 194C, the programming sequence is identical to that described above with reference to FIGS. 23 and 24.

In the next example programming session, the operator is described as replacing configuration file 157 of pump 4 (FIG. 9) with configuration file 141. Assume in this example that the operator really only intends to replace profile set 159 with profile set 143, but rather than using save to pump profile set button 194B (FIG. 10), the operator activates save to pump configuration file button 194A. As shown in FIG. 9, pump 4 is currently programmed to use Spanish and provide a bolus increment of 0.5. All of individual profiles 1 through 3 are depicted as being different from the corresponding individual profiles of profile set 143.

Figure 25:
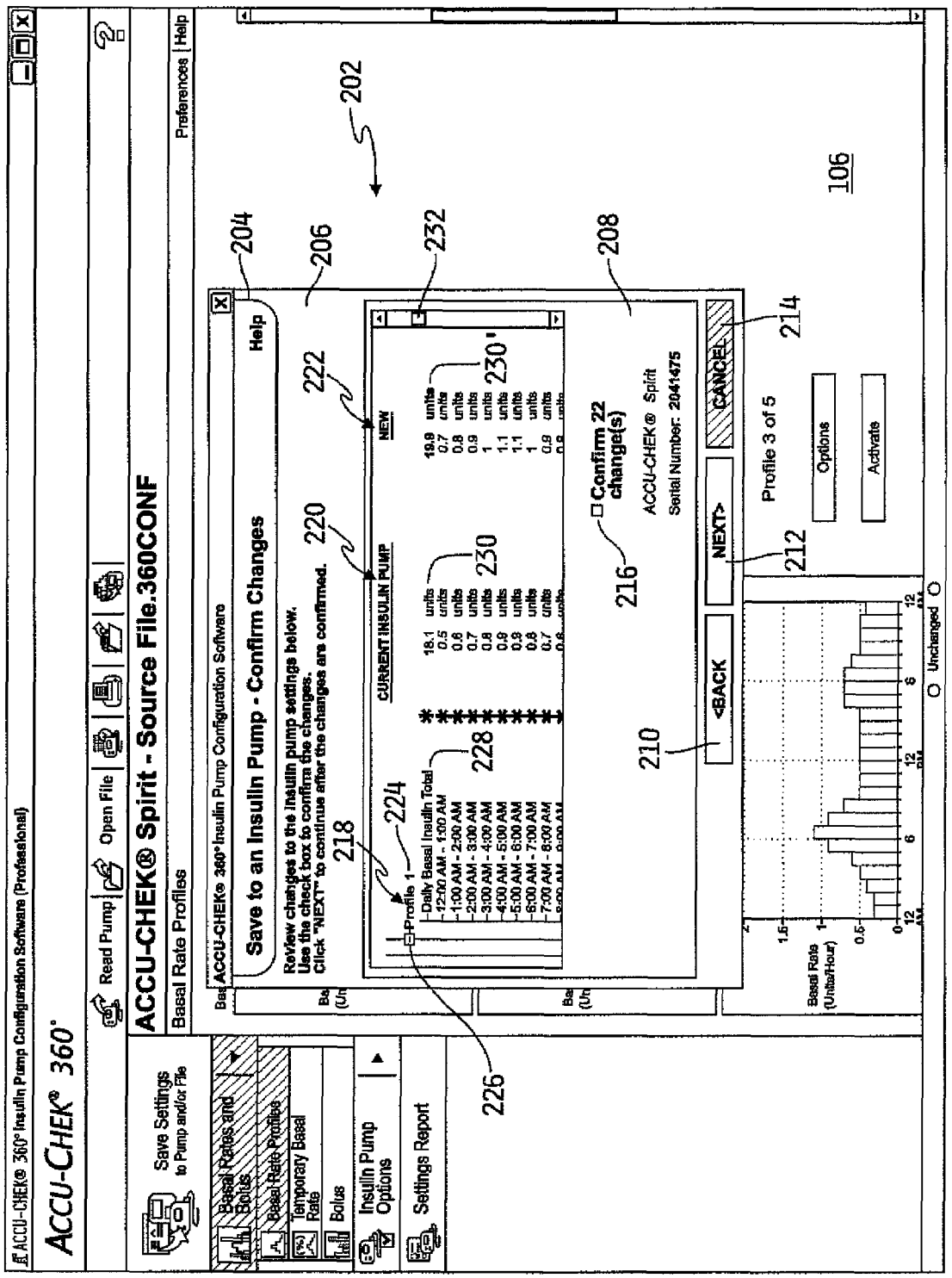
FIGS. 25 and 26 are screenshots similar to that of FIG. 11.
Figure 26:
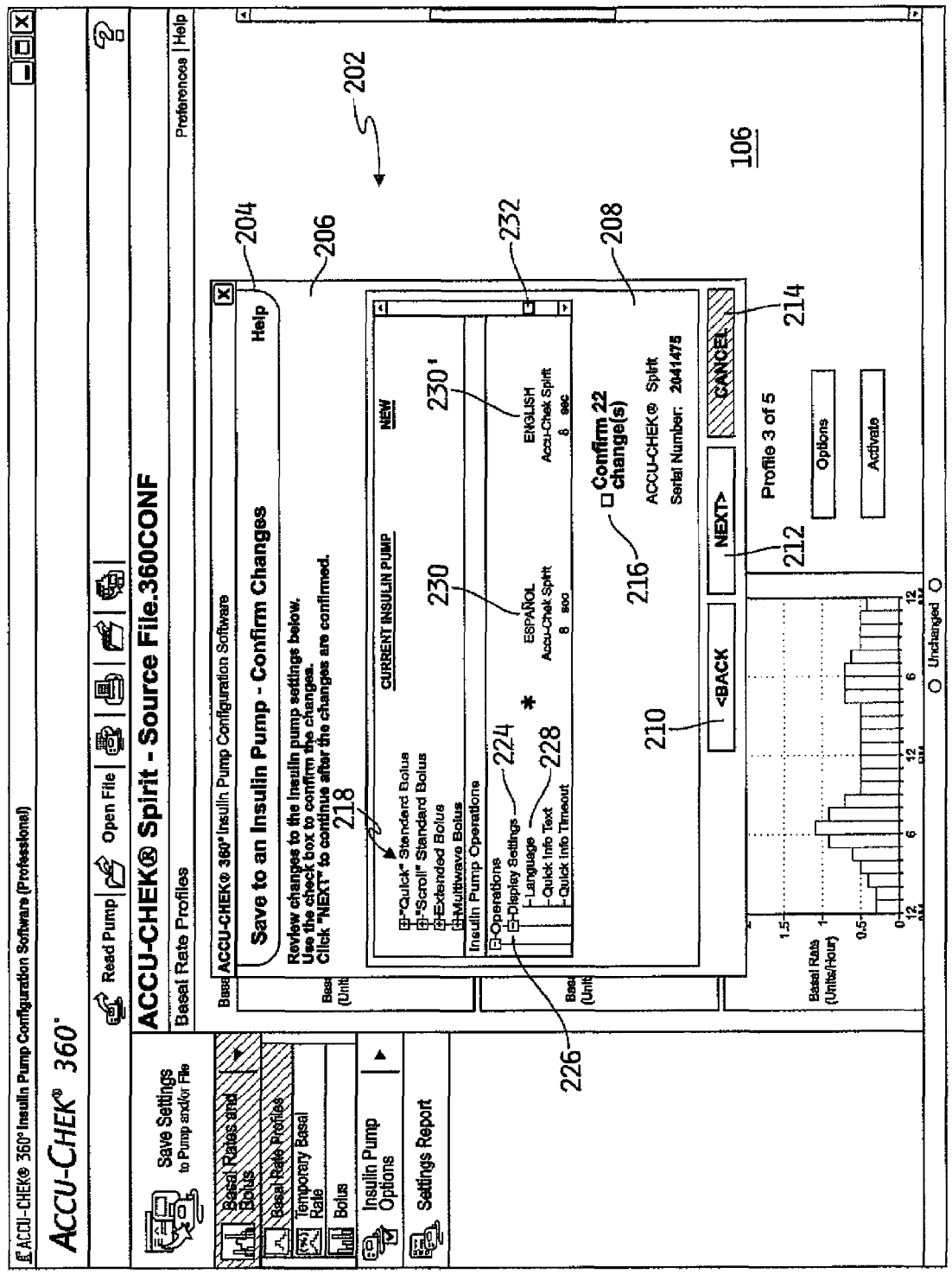

After the operator retrieves configuration file 141 in the manner described above, the operator activates save to pump configuration file button 194A (FIG. 10), instead of save to pump profile set button 194B. Software 17 then communicates with pump 4 (FIG. 11) and displays communication status dialog box 202 as shown in FIG. 25. Again, the most important changes to be made are automatically positioned for viewing in status window 208. Here, the changes to profile 1 are shown. If the operator used scrollbar 232 to scroll the content of status window 208, the operator could determine that the language option is about to be changed by viewing the screen as depicted in FIG. 26. In that case, the operator may realize that a language change is not desired, activate cancel button 214, and change the language option as described above before re-attempting to program pump 4.

For purposes of this example, assume that the operator scrolls down to review the changes to be made to profiles 2 and 3, and checks confirm changes box 216 without scrolling farther down to notice the language change. After activating next button 212 of FIG. 25, the operator is presented with critical change confirmation boxes 238 similar to those depicted in FIGS. 15 though 17 for confirmation of increases to be made to the profiles of profile set 159. After that, the programming process as described with reference to FIGS. 18 through 20 would be carried out, and the programming operation completed. Unfortunately, however, as this example illustrates, the operator inadvertently changed the language option of pump 4 from Spanish to English. As a result, the pump user, who may have visited the operator's office to have pump 4 programmed, may realize later in the day (after leaving the operator's office) that he or she is unable to operate pump 4.

Had the operator simply activated save to pump profile set button 196B, the above-described programming error would have been avoided. Of course, the operator could also have activated only profile set 143 (instead of entire configuration file 141) using open profile set button 138A (FIG. 4) and caused configuration file buttons 194A, 196A, and 198A to be disabled, thereby preventing the above-described error. It should further be understood with respect to all of the above-described examples, the operator may have chosen to activate configuration files, profile sets, or individual profiles from the pumps to be programmed using buttons 136A-C of read pump area 136, rather than retrieving configuration file 141 (or some portion thereof) from memory 15. Upon activating the pump information, the operator may make the desired modifications in the manner described above, and re-program the pump using buttons 194A-C of save to pump area 194 (FIG. 10).

Finally, with reference to FIG. 10, it should be understood that in addition to saving information to a pump as described above, the teachings of the present disclosure permit saving an active information set (i.e., a configuration file, a profile set, or an individual profile) to either a file or to both a pump and a file in one operation. Upon activating any one of buttons 196A-C of save to file area 196, the operator is presented with a screen similar to that depicted in FIG. 5 except that open file dialog box 144 is replaced with a similar save file dialog box (not shown). The operator can then select/define the location, name, and type of the file to be saved. Upon activating any one of buttons 198A-C of save to both area 198, the operator is first presented with the screen including a save file dialog box (not shown). After completing the file save, the operator is then guided through the various pump programming steps described above. In this manner, a backup file of the information being saved to a pump is made as part of the pump programming workflow, thereby reducing the steps required of the operator.

While an exemplary embodiment incorporating the principles of the present teachings has been disclosed hereinabove, the present teachings are not limited to the disclosed embodiments. Instead, this application is intended to cover any variations, uses, or adaptations of the disclosed general principles. Further, this application is intended to cover such departures from the present disclosure as come within known or customary practice in the art to which this application pertains and which fall within the limits of the appended claims.

What is claimed is:

1. A system for programming an insulin pump, including:
a computing device;
a communication link between the computing device and the insulin pump; and
software for execution by the computing device, the software being configured to facilitate retrieval of a source configuration file from a source location external to the insulin pump, the source configuration file including general configuration data including parameters that do not directly affect the timing and amount of insulin delivery of an insulin pump and a set of individual basal rate profiles, the software having a first mode wherein the source configuration file is written to a target configuration file having general configuration data and a set of individual basal rate profiles and being stored on the insulin pump, a second mode wherein the set of profiles of the source configuration file is written to the target configuration file without writing the general configuration data of the source configuration file, and a third mode wherein one of the profiles of the set of profiles of the source configuration file is written to the target configuration file without writing the general configuration data and the other of the profiles of the set of profiles of the source configuration file.

2. The system of claim 1, wherein the source location is a memory location of the computing device.

3. The system of claim 1, wherein the target configuration file includes a first configuration file stored on the insulin pump and a second configuration file stored in a memory location of the computing device.

4. A system for programming an insulin pump, including:
means for retrieving a source configuration file from a source location external to the insulin pump, the source configuration file including general configuration data including parameters that do not directly affect the timing and amount of insulin delivery of an insulin pump and a set of individual basal rate profiles;
means for saving the source configuration file to a target configuration file having general configuration data and a set of individual basal rate profiles, the target configuration file being stored on the insulin pump;
means for saving the set of individual basal rate profiles of the source configuration file to the target configuration file without writing the general configuration data of the source configuration file; and
means for saving one of the individual basal rate profiles of the set of individual basal rate profiles of the source configuration file to the target configuration file without writing the general configuration data and the other of the individual basal rate profiles of the set of individual basal rate profiles of the source configuration file.

* * * * *